(12) United States Patent
Di Domenico et al.

(10) Patent No.: US 10,976,316 B2
(45) Date of Patent: Apr. 13, 2021

(54) METHOD FOR CLASSIFYING MICROORGANISMS

(71) Applicant: BIOFILM CONTROL, Saint-Beauzire (FR)

(72) Inventors: Enea Gino Di Domenico, Rome (IT); Fabrizio Ensoli, Rome (IT); Luigi Toma, Rome (IT); Thierry Bernardi, Perignat les Sarlieve (IT); Christian Provot, Les Martes de Veyre (IT)

(73) Assignee: BIOFILM CONTROL, Saint-Beauzire (FR)

( * ) Notice: Subject to any disclaimer, the term of this patent is extended or adjusted under 35 U.S.C. 154(b) by 267 days.

(21) Appl. No.: 16/069,881

(22) PCT Filed: Jan. 5, 2017

(86) PCT No.: PCT/FR2017/050033
§ 371 (c)(1),
(2) Date: Jul. 12, 2018

(87) PCT Pub. No.: WO2017/121946
PCT Pub. Date: Jul. 20, 2017

(65) Prior Publication Data
US 2019/0120836 A1   Apr. 25, 2019

(30) Foreign Application Priority Data

Jan. 15, 2016  (FR) ...................................... 1650345
Mar. 31, 2016  (FR) ...................................... 1652784

(51) Int. Cl.
*G01N 33/569*  (2006.01)
*G01N 11/10*  (2006.01)
*G01N 35/00*  (2006.01)
*G01N 11/14*  (2006.01)

(52) U.S. Cl.
CPC ....... *G01N 33/56911* (2013.01); *G01N 11/10* (2013.01); *G01N 35/0098* (2013.01); *G01N 2011/147* (2013.01)

(58) Field of Classification Search
CPC ............. G01N 33/56911; G01N 11/10; G01N 35/0098; G01N 2011/147
See application file for complete search history.

(56) References Cited

FOREIGN PATENT DOCUMENTS

| FR | 2615621 A1 | 11/1988 |
| FR | 2866707 A1 | 8/2005 |
| FR | 2898363 A1 | 9/2007 |
| FR | 2916761 A1 | 12/2008 |
| FR | 2928656 A1 | 9/2009 |
| WO | 2012001312 A1 | 1/2012 |
| WO | 2013165615 A2 | 11/2013 |
| WO | 2014155020 A1 | 10/2014 |

OTHER PUBLICATIONS

Chavant, P. et al. A new device for rapid evaluation of biofilnn formation potential by bacteria. J. Microbiol. Methods (2007), doi: 10.1016/j.mimet.2006.11.010.*
Mahmoudabadi et al., Jundishapur J Microbiol. Jul. 2014; 7(7): e17105. Published online Jul. 1, 2014. doi: 10.5812/jjm.17105.*
An Sung Kwon et al. "Higher Biofilm Formation in Multidrug-Resistant Clinical Isolates of *Staphylococcus aureus*", Int J Antimicrob Agents 2008, 32:68-72.
Andres P. Staffer et al. "Alginate production affects *Pseudomonas aeruginosa* biofilm development and architecture but is not essential for biofilm formation", J Med Microbial Jul. 2004;53(Pt7):679-690.
Anthony J. Viera et al. "Understanding Interobserver Agreement: The Kappa Statistic", Fam Med May 2005;37(5):360-3.
BioFiles, Life Science vol. 3, No. 8, pp. 1-28.
C. I. Extremina et al. "Optimization of Processing Conditions for the Quantification of Enterococci Biofilms Using Microtitre-Plates", J. Microbial Meth 2011, 84, 167-173.
C. Suetens et al. "European surveillance of ICU-acquired infections (HELICS-ICU): methods and main results" Journal of Hospital Infection, val. 65, No. 2, pp. 171-173, 2007.
Carlos J. Sanchez Jr. et al. "Biofilm formation by clinical isolates and the implications in chronic infections", BMC Infect Dis. 2013; 29; 13:47.
Cédric Jacqueline et al. "Impact of Bacterial Biofilm on the Treatment of Prosthetic Joint Infections" J Antimicrob Chemother 2014;69:137-140.
D. Djordjevic et al. "Microtiter Plate Assay for Assessment of Listeria Monocytogenes Biofilm Formation", App Env Microbial, 2002, 68 (6), 2950-2958.
D. Lindsay et al. "Bacterial biofilms within the clinical setting: what healthcare professional should know", J Hasp Infect 2006; 64: 4, 313-325.
D. Yang et al. "Biofilm-forming Klebsiella pneumoniae strains have greater likelihood of producing extended-spectrum β-lactamases", J Hasp. Infect. 2008, 68, 369-371.
E. Yoko Furuya et al. "Antimicrobial Strategies for the Prevention and Treatment of Cardiovascular Infections" Curr Opin Pharmacal 2003,3 (5):464-469.
Elke Peeters et al. "Comparison of multiple methods for quantification of microbial biofilms grown in microtiter plates", J Microbial Methods. Feb. 2008;72(2):157-165.
Elodie Olivares et al. "The Biofilm Ring Test®: a rapid method for the routine analysis of *P. aeruginosa* biofilm rormation kinetics" JCM Accepted Manuscript Posted Online Dec. 30, 2015. J. Clin. Microbial. doi:10.1128/JCM.02938-15.

(Continued)

*Primary Examiner* — Kade Ariani
(74) *Attorney, Agent, or Firm* — Cantor Colburn LLP

(57) ABSTRACT

The present invention relates to a method for determining the biofilm-forming capacity of microorganisms. The present invention also relates to a method for classifying microorganisms according to the biofilm-forming capacity thereof. In particular, the present invention is useful in the fields of analysis, biological and enzymological research, pharmaceuticals, diagnostics and/or medicine. The present invention is also useful in the clinical, environmental and food-processing fields.

16 Claims, 4 Drawing Sheets

(56) References Cited

OTHER PUBLICATIONS

Fiona Stapleton et al. "Bacterial Adherence and Glycocalyx Formation on Unworn Hydrogel Lenses", J Brit Contact Lens Assoc. 1993;16:113-117.
Friedrich Götz "*Staphylococcus* and Biofilms", Mol Microbial 2002; 43: 1367-1378.
Gordon D. Christensen et al. "Adherence of Coagulase-Negative Staphylococci to Plastic Tissue Culture Plates: a Quantitative Model for the Adherence of Staphylococci to Medical Devices", J. CM. Microbial. 22,996-1006.
Herbert O. Gbejuade et al. "The Role of Microbial Biofilms in Prosthetic Joint Infections—A Review", Acta Orthopaedica 2015; 86 (2): 147-158.
J. Andy Schaber et al. "Analysis of quorum sensing-deficient clinical isolates of Pseudonmonas aeruginosa", J Med Microbial 2004;53:841-853.
J. Dissemond. "When is a Wound Chronic", Hautarzt 2006; 57: 55.
J. W. Costerton et al. "Bacterial Biofims: A Common Cause of Persistent Infections", Science, 1999, 284:1318-1322.
James P. O'Gara et al. "*Staphylococcus epidermidis* biofilms: importance and implications", J Med Microbial. 2001; 50:582-587.
Jeff G. Lied et al. "The Exopolysaccharide Alginate Protects Pseudomonas aeruginosa Biofilm Bacteria from IFN-y-Mediated Macrophage Killing", J Immunol Dec. 1, 2005;175(11):7512-8.
Joe Latimer et al. "Attenuated Virulence and Biofilm Formation in *Staphylococcus aureus* Following Sublethal Exposure to Triclosan", Antimicrob Agents Chemother. Jun. 2012:56(6):3092-3100.
Judith H.Merritt et al. "Growing and Analyzing Static Biofilms" Curr Protoc Microbial. Jul. 2005: 0 1: Unit-1B.1. doi:10.1002/9780471729259.mc01b01s00.
Ken Welch et al. "A Method for Quantitative Determination of Biofilm Viability", J Funct. Biomater. 2012, 3, 418-431.
Laurence G. Rahme et al. "Common Virulence Factors for Bacterial Pathogenicity in Plants and Animals", Science. 1995:268:1899:902.
Lavin A. Joseph et al. "Expression of Vibrio vulnificus Capsular Polysaccharide Inhibits Biofilm Formation" J Bacterial, 2004, 186 (3) 889-893.
Livnat Naparstek et al. "Biofilm formation and susceptibility to gentamicin and colistin of extremely drug-resistant KPC-producing Klebsiella pneumoniae", J Antimicrob Chemother, 2014;;69(4): 1027-34.
M. P. Ryan et al. "*Ralstonia* spp.: emerging global opportunistic pathogens", Eur J Clin Microbial Infect Dis. 2014.
Malena Elise Skogman et al. "Combining biofilm matrix measurements with biomass and viability assays in susceptibility assessments of antimicrobials against *Staphylococcus aureus* biofilms", J Antibiot (2012) 65, 453-459.
Massimo Marroni et al. "Outbreak of Infusion-Related Septicemia by Ralstonia Pickettii in the Oncology Department", Tumori 2003; 89: 575-576.
Mathias Müsken et al. "A 96-well-plate-based optical method for the quantitative and qualitative evaluation of *Peudomonas aeruginosa* biofilm formation and its application to susceptibility testing", Nature Protocols (2010), 5(8) 1460-1469.
Michael Otto "*Staphylococcal* Biofilms" Curr Top Microbial Immunol 322:207-228.
Michael Otto, Ph.D. "*Staphylococcus epidermidis*-the "accidental" pathogen", Nat Rev Microbiol. Aug. 2009; 7(8): 555-567.
Michael R. Benoit et al. "New Device for High-Throughput Viability Screening of Flow Biofilms" Microbiology & Immunology Department, Applied and Environmental Microbiology, Jul. 2010, vol. 76, No. 13, pp. 4136-4142.
Niels Høiby et al. "Antibiotic Resistance of Bacteria Biofilms", Int J Antimicrob Agents 201 Ob; 35(4): 322-332.
Niels Høiby et al. "Pseudomonas aeruginosa Biofilms in Cystic Fibrosis", Future Microbiology. 2010a, 5:1663-1674.
Niels Høiby et al. "The Clinical Impact of Bacterial Biofilms", Int J Oral Sci 2011; 3(2): 55-65.

NIH Parent Grant Announcement, 2002. Research on Microbial Biofilms. NIH website. Available: http://grants.nih.gov/grants/guide/pa-files/PA-03-047.html. Accessed Sep. 2, 2014.
Nuno Cerca et al. "Comparative assessment of antibiotic susceptibility of coagulase-negative staphylococci in biofilm versus planktonic culture as assessed by bacterial enumeration or rapid XTT colorimetry", J of Antimicrob Chemother, Aug. 2005, 56:331-336.
Nyambura Moremi et al. "Predominance of multi-resistant gram-negative bacteria colonizing chronic lower limb ulcers (CLLUs) at Bugando Medical Center", BMC Res Notes. Apr. 4, 2014;7:211.
Patrick Chavant et al. "A new device for rapid evaluation of biofilm formation potential by bacteria", J Microbial Methods, 2007, 68, 605-612.
Peter Esser et al. "Principles in Adsorption to Polystyrene" Thermo Scientific Technical Bulletin B06a.
Pradeep K. Singh et al. "Quorum-sensing signals indicate that cystic fibrosis lungs are infected with bacterial biofilms", Nature 2000, 407, 762-764.
Qian Wang et al. "Enhancement of Biofilm Formation by Subinhibitory Concentrations of Macrolides in icaADBC-Positive and -Negative Clinical Isolates of *Staphylococcus epidermidis*", Antimicrob Agents Chemother 2010, 54:2707-2711.
R. Podschun et al. "*Klebsiella* spp. As Nosocomial Pathogens: Epidemiology, Taxonomy, Typing Methods, and Pathogenicity Factors", Clin Microbial Rev 1998, 11:589-603.
R. Srinivasa Rao et al. "Correlation between biofilm production and multiple drug resistance in imipenem resistant clinical isolates of acinetobacer baumannii", Indian J Med Microbial 2008, 26:333-337.
Rabih O. Darouiche M.D. "Treatment of Infections Associated with Surgical Implants". N. Engl. Med. 2004; 350: 1422-1429.
Robert H. K. Eng et al. "Inoculum Effect of New β-Lactam Antibiotics of Pseudonmonas aeruginosa", Antimicrob Agents Chemother. 1984; 26(1) :42-7.
Niels Høiby et al. "Pseudomonas aeruginosa Biofilms in Cystic Fibrosis", Future Microbiology. 2010, 5:1663-1674.
G. Besciak et al. "Biofilm as a Basic Life Form of Bacteria", Environmental Biotechnology Department, Jan. 1, 2012, pp. 1-5, url:https://www.seed.abe.kth.se/polopoly_fs/1.651085!/JPSU17P13.pdf.
International Search Report dated Apr. 26, 2017 re: Appication No. PCT/FR2017/050033, pp. 1-6.
Joe J. Harrison et al. "Microtiter susceptibility testing of microbes growin on peg lids: miniaturized biofilm model for high-throughput screening", Nature Protocols, Jun. 10, 2010, vol. 5, No. 7, pp. 1236-1254, XP055319778.
M.C. Martin-Espada et al. "Peracetic acid disienfectant efficacy against Psuedomonas aeruginosa biofilms on polystyrene surfaces and comparison between methods to measure it", LWT—Food Science and Technology, , Apr. 2014, vol. 56, No. 1, pp. 58-61, XP028800477.
Majed M. Masadeh et al. "In vitro determination of the antibiotic susceptibility of biofilm-forming *Pseudomonas aeruginosa* and *Stpahylococcus aureus*: possible role of proteolytic activity and membrane lipopolysaccharide", Infection and Drug Resistance, DOVEPRESS, Mar. 1, 2013, pp. 1-6.
Rodney M. Donlan. "Biofilms and Device-Associated Infections", Emerg Infect Dis 2001; 7(2): 277-81.
S. Brook Peterson et al. "Different Method for Culturing Biofilms in Vitro", ResearchGate, Oct. 5, 2010, pp. 251-266 https://www.researchgate.net/publication/24102040, XP055319766.
S. Sangetha et al. "In situ Tem and Sem Studies on the Antimicrobial Activity and Prevention of Candida Albicans Eliofilm by Cassia Spectabilis Extract" Micron (2009) 40, 439-443.
Sander Croes et al. "*Staphylococcus aureus* Biofilm Formation at the Physiologic Glucose Concentration Depends on the *S. aureus* Lineage". BMC Microbial. 2009; 28; 9:229.
Saravanan Periasamy et al. "How *Staphylococcus aureus* Biofilms Develop Their Characteristic Structure", Pro Natl Acad Sci USA. 2012; 24;109(4):1281-6.
Srdjan Stepanovic et al. "A Modified Microtiter-Plate Test for Quantification of *Staphylococcal* Biofilm Formation", J Microbial Methods. 2000;40:175-179.

(56) References Cited

OTHER PUBLICATIONS

Steven M. Kurtz, Ph.D. et al. "Economic Burden of Periprosthetic Joint Infection in the United States", J Arthroplasty, 2012, 27(8) 61-65.

Thierry De Baere et al. Classification of Ralstonia Picketttii Biovar 3/'Thomosii' Strains (PICKETT 1994) and of New Isolates Related to Nosocomial Recun-ent Meningitis as *Ralstonia mannitolytica* sp. nov. Int J Syst Evol Microbial. 2001; 51: 547-58.

Tom Coenye et al. "Use of PCR Analyses to Define the Distribution of *Ralstonia* Species Recovered from Patients with Cystic Fibrosis" J. Clin. Microbail. 2005, 43:3463-3466.

U. Römling et al. "Biofilm Infections, Their Resilience to Therapy and Innovative Treatment Strategies", J Intern Med 2012 272(6):541-561.

Wang Hengzhuang et al. "In Vivo Pharmacokinetics/Pharmacodynamics of Colistin and Imipenem in Pseudomonas aeruginosa Biofilm Infection", Antimicrob Agents Chemother 2012; 56(5): 2683-2690.

William Costerton et al. "The Application of Biofilm Science to the Study and Control of Chronic Bacterial Infections", J. Clin Invest. 2003;112:1466-1477.

Youwen Pan et al. "Synergistic Effects of Sodium Chloride, Glucose, and Temperature on Biofilm Formation by Listeria monocytogenes Serotype 1/2a and 4b Strans" Appl Env Microbial, 2010, 76 (5), 1433-1441.

Yue-Qing Zhang et al. "Genome-Based Analysis of Virulence Genes in a Non-Biofilm-Forming *Staphylococcus epidermidis* Strain (ATCC 12228)", Molecular Microbial. Sep. 2003;49(6):1577-1593.

Yves De Gheldre et al. "Evaluation of Oxoid Combination Discs for Detection of Extended-Spectrum β-Lactamases", J. Antimicrob Chemother Oct. 2003;52(4):591-7.

\* cited by examiner

METHOD FOR CLASSIFYING MICROORGANISMS

TECHNICAL FIELD

The disclosure relates to a process for determining the biofilm-producing capacity of a microorganism.

The disclosure also relates to a process for classifying microorganisms as a function of their biofilm-producing capacity.

The disclosure finds its application especially to the fields of analysis, of biological research, of enzymological research, in the pharmaceuticals domain, in the field of diagnosis and/or in the medical domain. The disclosure is also applicable to the clinical, environmental or food-processing domain.

BACKGROUND

The formation of a biofilm is a key property of bacteria, enabling long-term survival both in natural ecosystems and animal hosts (Høiby, 2010b). In fact, bacteria that grow in a biofilm matrix are intrinsically more resistant to agents from the environment and also antimicrobial agents, compared to growing planktonic cells. Bacterial biofilms represent a serious problem in industry and medicine, including surgery and dentistry, where they frequently cause chronic and recurrent infections (Lindsay, 2006). Gram-positive and Gram-negative bacteria are both capable of forming a biofilm (Donlan, 2001). It has been estimated that up to 80% of human infectious diseases which have a significant impact on morbidity and healthcare costs for patients are associated with biofilms (Romling, 2012; NIH Parent Grant Announcement, 2002). The formation of biofilms on implantable medical devices causes persistent infections which represent more than 60% of reported nosocomial infections (Darouiche, 2004). In this context, infections associated with catheters represent the most serious and costly undesirable event caused by a biofilm produced by bacteria, frequently leading to failed treatment and requiring the removal of the medical device (Costerton et al, 2003). Typical examples of diseases associated with biofilms include "difficult" infections such as bone and joint infections, caused by *Staphylococcus aureus* which is a strongly biofilm-producing bacterium (Kurtz, et al., 2012, Jacqueline, 2014, Gbejuade, 2015), infectious endocarditis caused mainly by staphylococci or streptococci, which is associated with high mortality rates (Furuya, 2003) and infections affecting patients suffering from cystic fibrosis, in which *P. aeruginosa* causes chronic pulmonary infections and respiratory failure (Singh, 2000; Høiby, 2010a).

Antibiotic treatment, which is either empirical or based on drug sensitivity testing, is often unable to control difficult infections associated with biofilms such as in the case of infection on medical devices (Høiby, 2010a). Indeed, profiles of resistance to traditional antibiotics are produced based on microorganisms in planktonic growth. Thus, in vitro susceptibility to antibiotics does not take into account the production of biofilms and may not be representative of the in vivo resistance of the bacteria to medications (Costerton et al., 1999). Consequently, new laboratory tests capable of evaluating biofilm production and the susceptibility to antibiotics of the microorganisms' biofilm formation are necessary and desirable in addition to routine microbiology tests in order to effectively target difficult infectious agents.

There is therefore a real need to find a novel process that makes it possible to evaluate the production of a biofilm by a microorganism and also any potential susceptibility thereof, in the formation of the biofilm or the biofilm formed, to antibiotics.

In addition, there is a real need to find a process that is easy to carry out and makes it possible to rapidly characterize the biofilm-producing capacity of the microorganism.

An ideal diagnostic technique must be capable of providing rapid identification of the microorganism(s), in order to help to guide suitable antimicrobial therapy.

A variety of direct or indirect quantitative methods have been developed for evaluating the ability of bacterial strains to adhere to surfaces (Peeters, 2008), either based on colorimetry (Stepanovic, 2000; Joseph, 2004) or on microscopic techniques (Sangetha, 2009; Currently, crystal violet (CV) staining is the most widely used method for the in vitro quantification of biofilms, due to its relative simplicity and sensitivity (Christensen, 1985; Stepanovic, 2000). However, this method has significant limitations. In fact, at least 24/48 hours of incubation and repeated treatment measurements are necessary, leading to results with a large standard deviation, and making the method neither easy to carry out for standardization or suitable for large-scale screening in a clinical context. In addition, this method gives results for MIC for eradicating a biofilm after 24/48 hours that involve very high concentrations of antibiotics that are not clinically relevant. In other words, the minimum inhibitory concentrations (MICs) are so high that they cannot be used clinically. Recently, a new technology, namely the Biofilm Ring Test® (BFRT), has been proposed for the evaluation of bacterial biofilms. The principle is based on the immobilization of magnetic beads by the biofilm matrix that is growing in vitro (Chavant, 2007). This process does not require extensive handling (for example does not require steps of washing or of staining), which thereby ensures reproducibility of the results and reduces the standard deviation, which is a positive criterion for standardizing procedures. Thus, BFRT represents a promising tool for detecting a biofilm in a clinical context. Nonetheless, this process only makes it possible to determine the presence or absence of a biofilm. In addition, this process does not make it possible, especially in a single determination operation, to provide direct information on the "dynamics" and the "power" of a microorganism to produce biofilm, in particular compared to a reference standard from microbial isolates.

Indeed, the initial procedure may require repeat measurements, carried out at different times, in order to estimate the microbial biofilm formation, constituting another significant limitation to routine use in laboratory tests.

There is therefore a real need to find a means/process making it possible to determine the biofilm-producing capacity/dynamics of a microorganism.

There are also processes, especially for diagnostic applications, making it possible to determine the capacity of antibiotics to inhibit biofilm formation. This is especially the antibiofilmogram (registered trademark) process, in a format in which for example 11 antibiotics, at 8 different doses, are ready to use in microplates (Olivares, 2015). Nonetheless, this known process that is commonly used in diagnosis does not make it possible to characterize or determine the biofilm-producing capacities of microorganisms.

There is therefore a real need to find a process that overcomes these drawbacks, disadvantages and obstacles of the prior art, in particular a process making it possible especially to determine the biofilm production and to determine the biofilm-producing capacity of a microorganism, making it possible for example to adapt the treatment processes as a function of the microorganism's characteristics.

In addition, there is a real need to find a simple, inexpensive and clinically applicable process that makes it possible to evaluate especially the potential biofilm-producing capacity of a microorganism.

There is also a real need to find a means/process that makes it possible to determine the biofilm-producing capacity of a microorganism in a short period of time.

BRIEF SUMMARY

The disclosure makes it possible to solve these problems and disadvantages of the prior art by providing a process for determining the biofilm-producing capacity of a microorganism, comprising the following steps:

a) introducing at least two particles into culture containers comprising a liquid culture medium suited to the growth of said microorganism, said particles resting on a surface submerged in the culture medium, b) introducing and independently inoculating the culture medium of the containers obtained in step a) with said microorganism at a concentration preferentially of from $1\times10^{-1}$ to $1\times10^{-6}$ McFarland (McF), each medium independently comprising a different concentration of microorganisms, c) maintaining the inoculated culture media in conditions which enable growth of said microorganism, d) applying a field capable of moving said at least two particles resting on a surface submerged in the culture medium, in order for them to aggregate preferentially in spot form, e) determining the biofilm-producing capacity of the microorganism by observing and/or measuring the aggregation of said particles as follows:

the absence of aggregation of said particles appearing at a concentration of from $1\times10^{-6}$ to $1\times10^{-4}$ McF corresponding to a strongly biofilm-producing microorganism, the absence of aggregation of said particles appearing from a concentration of greater than $1\times10^{-4}$ and less than $1\times10^{-2}$ McF corresponding to a moderately biofilm-producing microorganism, the absence of aggregation appearing from a concentration of greater than or equal to $1\times10^{-2}$ McF corresponding to a weakly biofilm-producing microorganism, an aggregation of said particles, regardless of the concentration, corresponding to a non-biofilm-producing microorganism.

The inventors have demonstrated, surprisingly, that the process according to the disclosure advantageously makes it possible, in a very short time, for example less than 6 hours, to determine the biofilm-producing capacity of a microorganism and/or to classify microorganisms as a function of their biofilm-producing capacity.

In particular, the inventors have demonstrated, in accordance with general knowledge, that there are at least four categories of microorganisms, namely especially microorganisms that do not produce biofilm, microorganisms that produce relatively little biofilm (weakly-producing), microorganisms that produce a moderate amount of biofilm (moderately-producing) and microorganisms that are strongly biofilm-producing.

The inventors have also demonstrated, surprisingly, that the process according to the disclosure relies on measuring the biofilm formation at an early stage. In particular, they have demonstrated that, in a given period of time, for example 5 hours, the lower the initial concentrations of microorganisms, for example of bacterial cells, which may inhibit the movement/aggregation of particles, the greater is their capacity for producing a biofilm. Conversely, if high concentrations of microorganisms, for example bacteria, are not capable of preventing the movement/aggregation of microparticles, they are considered to be low-risk/non-biofilm-producing. In addition, the inventors have evaluated and demonstrated the biofilm formation capacity/characterization of two Gram-positive and Gram-negative clinical isolates and compared this to those of laboratory strains with known biofilm phenotypes and also for negative controls, used as internal reference, in order to ensure the preciseness and reproducibility of the results. Inter-assay reproducibility was determined by comparison with the crystal violet (CV) staining assay. The inventors demonstrated that the results obtained regarding the characterization of the microorganisms agree with those obtained by customary techniques such as crystal violet staining in a much shorter period of time, for example 5 to 10 times shorter.

In addition, the inventors have demonstrated, surprisingly, that the process of the disclosure makes it possible to obtain a reliable and reproducible result with similar, or even superior, specificity to that of the customary processes.

Moreover, the process according to the disclosure advantageously makes it possible to dispense with non-specific results, especially associated with the production of mucus by the microorganisms, unlike customary processes, especially based on visualization with stains such as crystal violet, which is known to stain mucus and bacteria, thereby overestimating the presence of biofilm and/or being the source of false positive results. In particular, the processes based on visualization with stains such as crystal violet do not therefore precisely quantify the bacterial biomass.

Another subject of the present disclosure is a process for classifying microorganisms, comprising the following steps:

a) introducing at least two particles into culture containers comprising a liquid culture medium suited to the growth of said microorganism, said particles resting on a surface submerged in the culture medium, b) introducing and independently inoculating the culture medium of the containers obtained in step a) with said microorganism at a concentration of from $1\times10^{-1}$ to $1\times10^{-6}$ McF, each medium independently comprising a different concentration of microorganisms, c) maintaining the inoculated culture media in conditions which enable growth of said microorganism, d) applying a field capable of moving said at least two particles resting on a surface submerged in the culture medium, in order for them to aggregate preferentially in spot form, e) classifying the microorganism by observing and/or measuring the aggregation of said particles as follows:

category I: absence of aggregation of said particles appearing at a concentration of from $1\times10^{-6}$ to $1\times10^{-4}$ McF corresponding to a strongly biofilm-producing microorganism, category II: absence of aggregation of the particles appearing from a concentration of greater than $1\times10^{-4}$ and less than $1\times10^{-2}$ McF corresponding to a moderately biofilm-producing microorganism, category III: absence of aggregation appearing from a concentration of greater than or equal to $1\times10^{-2}$ McF corresponding to a weakly biofilm-producing microorganism, category IV: aggregation of the particles, regardless of the concentration, corresponding to a non-biofilm-producing microorganism.

In the present document, McFarland unit (McF) is intended to mean the international unit known to those skilled in the art, for example as described especially in the document "National Committee for Clinical Laboratory Standards", 2001 and 2003.

In the present document, one McFarland unit corresponds to approximately $3.10^8$ bacteria/ml, a dilution of $1\times10^{-6}$ McF therefore corresponds to $3.10^2$ bacteria/ml. For example, quantitatively, roughly 60 bacteria per 200 µl, for example used to inoculate microplate wells in the described process.

According to the disclosure, "strongly biofilm-producing" is intended to mean a microorganism capable of synthesizing a sufficient amount of biofilm to prevent the aggregation of particles during the application of the field, after maintaining the culture medium for a given period of time. This may for example be a microorganism capable of synthesizing a sufficient amount of biofilm to prevent the aggregation of the particles, from an inoculum of the order of 60 to 6000 bacteria, considered to be very weak by those skilled in the art.

According to the disclosure, "moderately biofilm-producing" is intended to mean a microorganism capable of synthesizing a sufficient amount of biofilm to prevent the aggregation of particles during the application of the field, for a given period of time after maintaining the culture medium, from an inoculum of the order of 6000 ($6.10^3$) to $6.10^5$ bacteria, considered to be standard by those skilled in the art.

According to the disclosure, "weakly biofilm-producing" is intended to mean a microorganism capable of synthesizing a sufficient amount of biofilm to prevent the aggregation of particles after maintaining the culture medium for a given period of time, from an inoculum of greater than $6\times10^7$ bacteria, considered to be strong by those skilled in the art.

In other words, a "strongly biofilm-producing" microorganism is a microorganism which, after culture from a weak concentration of microorganisms, for example of from $1\times10^{-6}$ to $1\times10^{-4}$ McF, prevents/hinders the movement of the particles while the process is being carried out, preventing them coming together/aggregating, especially in spot form.

In other words, a "moderately biofilm-producing" microorganism is a microorganism which, after culture from a moderate concentration of microorganisms, for example of greater than $1\times10^{-4}$ and less than $1\times10^{-2}$ McF, prevents/hinders the movement of the particles while the process is being carried out, preventing them coming together/aggregating, especially in spot form.

In other words, a "weakly biofilm-producing" microorganism is a microorganism which, after culture from a strong concentration of microorganisms, for example from a concentration of greater than or equal to $1\times10^{-2}$ McF, prevents/hinders the movement of the particles while the process is being carried out, preventing them coming together/aggregating, especially in spot form.

In other words, a "non-biofilm-producing" microorganism is a microorganism which, after culture, regardless of the concentration of microorganisms, has no effect on the movement of the particles while the process is being carried out, and enables aggregation of the particles.

According to the disclosure, the inoculated culture media may be maintained for 1 to 24 hours, preferably 1 to 8 hours, preferably 4 to 6 hours. Those skilled in the art, from their general knowledge, will know how to adapt the maintenance time as a function of the microorganism.

Advantageously, the inoculated culture media may be maintained for 4 to 6 hours.

Advantageously, maintaining the culture media for 4 to 6 hours makes it possible, while the process of the disclosure is being carried out, to draw conclusions regarding the production capacity of the microorganism and/or its classification according to the disclosure.

Advantageously, the inventors have demonstrated that maintaining the culture media in step c) for 4 to 6 hours advantageously makes it possible, when the microorganism has been inoculated at a concentration of from $1\times10^{-1}$ to $1\times10^{-6}$ McF, to draw conclusions regarding the production capacity of the microorganism and/or the classification thereof according to the disclosure.

According to the disclosure, the inoculated culture media may be maintained for 5 to 12 generation times of the microorganism, preferably from 6 to 10 generation times of the microorganism.

Those skilled in the art, due to their general knowledge, know the generation time, that is to say the time taken for a population of microorganisms to double. For example, this may be the time mentioned in the document "Microbiochimie et alimentation" [*Microbiochemistry and food*], Alain Branger, Educagri Editions, 2012. For example, the generation time of a bacterium may be on average 30 minutes.

According to the disclosure, the culture container may be any culture container known to those skilled in the art and/or suitable commercially available culture container. It may for example be a well of a 96-well plate and/or of any culture reactor known to those skilled in the art. Preferentially, the culture container may be formed of a material which promotes adhesion of the microorganisms, for example made of polystyrene (Thermo Scientific Technical Bulletin B06a Principles in adsorption to polystyrene, 2010), or may be modified in order to promote adhesion thereof, for example by irradiation of the culture container, for example by irradiation of a polystyrene container (Biofiles, issue 3.8, 21-24).

The culture container may advantageously be a planar and/or flat-bottomed container. Advantageously, when the culture container is planar and/or flat-bottomed, the particles aggregate on the planar surface and/or the flat bottom.

According to the disclosure, the process of the disclosure may be carried out in a plurality of culture containers. For example, the process of the disclosure may be carried out in at least 6 culture containers, for example wells of 96-well microplates, or another format.

This may for example be culture containers made of polystyrene, polypropylene, polycarbonate or glass.

Those skilled in the art, from their general knowledge, will know how to adapt/choose the container as a function of the microorganism.

According to the disclosure, when the process comprises 6 culture containers, it may comprise independently in each container an identical culture medium comprising different concentrations of microorganisms. For example, said containers may comprise, respectively, a concentration of microorganisms of $1\times10^{-6}$ McF, $1\times10^{-5}$ McF, $1\times10^{-4}$ McF, $1\times10^{-3}$ McF, $1\times10^{-2}$ McF and $1\times10^{-1}$ McF. An additional container may also be added, containing all the constituents of the medium with the exception of the microorganism, thereby representing a control for aggregation of the particles, or reference.

According to the disclosure, liquid culture medium is intended to mean any liquid culture medium known to those skilled in art and/or commercially available, in which at least one microorganism is capable of growing. It may for example be a natural or synthetic medium. It may for example be BHI (brain heart infusion), Mueller-Hinton medium, or glucose broth. Those skilled in the art, from their general knowledge, will know how to choose the suitable culture medium as a function of the microorganism.

According to the disclosure, the microorganism may be any microorganism known to those skilled in the art. It may be a prokaryotic cell, for example a bacterium, or a eukaryotic cell, for example a fungus or yeast. It may for example be *Candida, Cryptococcus, Malassezia, Pityrosporum, Pneumocystis, Epidermo-phyton, Microsporum, Trichophyton*. It may for example be a protozoan, for example *Entamoeba histolytica, Acanthamoeba castellanii, Naegleria fowleri*.

Among the prokaryotic cells, it may for example be any bacterium known to those skilled in the art, for example the bacteria included in the group, without being limited thereto, consisting of *Acetobacter aurantius, Actinobacillus actinomycetemcomitans, Agrobacterium tumefaciens, Azorhizobium caulinodans, Azotobacter vinelandii, Bacillus anthracis, Bacillus brevis, Bacillus cereus, Bacillus fusiformis, Bacillus licheniformis, Bacillus megaterium, Bacillus stearothermophilus, Bacillus subtilis, Bacteroides gingivalis, Bacteroides melaninogenicus, Bartonella henselae, Bartonella quintana, Bordetella bronchiseptica, Bordetella pertussis, Borrelia burgdorferi, Branhamella catarrhalis, Brucella abortus, Brucella melitensis, Brucella suis, Burkholderia mallei, Burkholderia pseudomallei Calymmatobacterium granulomatis, Campylobacter coli, Campylobacter jejuni, Campylobacter pylori, Chlamydia pneumoniae, Chlamydia psittaci, Chlamydia trachomatis, Chlamydophila pneumoniae, Chlamydophila psittaci, Clostridium botulinum, Clostridium difficile, Clostridium perfringens, Clostridium tetani, Clostridium welchii, Corynebacterium diphtheriae, Corynebacterium fusiforme, Coxiella burnetii Ehrlichia chaffeensis, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis Haemophilus ducreyi, Haemophilus influenzae, Haemophilus parainfluenzae, Haemophilus pertussis, Haemophilus vaginalis, Helicobacter pylori, Klebsiella pneumoniae, Klebsiella rhinoscleromatis-Klebsiella oxytoca, Lactobacillus acidophilus, Lactobacillus casei, Lactococcus lactis, Legionella pneumophila, Methanobacterium extroquens, Microbacterium multiforme, Micrococcus luteus, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma pneumoniae Neisseria gonorrhoeae, Neisseria meningitidis, Nocardia asteroides Pasteurella multocida, Pasteurella tularensis, Porphyromonas gingivalis, Pseudomonas aeruginosa, Pseudomonas maltophilia, Rhizobium radiobacter, Rickettsia prowazekii, Rickettsia mooseri, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Staphylococcus aureus, Staphylococcus epidermidis, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema pallidum, Vibrio cholerae, Vibrio comma, Vibrio parahemolyticus, Vibrio vulnificus, Xanthomonas maltophilia Yersinia enterocolitica, Yersinia pestis* and *Yersinia pseudotuberculosis*, etc.

According to the disclosure, in the case of the use of anaerobic bacteria, the conditions for the anaerobic culture of the microorganism will be able to be obtained by blocking the open end of the culture reactor, for example using parafilm, a stopper, etc., or by placing said reactor under conditions that enable the growth of anaerobic bacteria. This may be for example anaerobic jars, pouches that generate an oxygen-depleted and carbon dioxide-enriched atmosphere, anaerobic chambers with a controlled atmosphere, and/or any suitable means known to those skilled in the art.

According to the disclosure, said at least two particles may be selected from the group comprising an electrically charged particle, a magnetic particle, a particle coated with at least one magnetic layer, a magnetizable particle, a particle coated with a magnetizable layer, or a mixture of two or more of these particles. In fact, it may be any particle which makes it possible to carry out the present disclosure.

According to the disclosure, the particles may rest on a surface submerged in the culture medium. Said particles are in a stable position, that is to say at rest, in the absence of the magnetic, or electric, or electromagnetic, field. Advantageously, said particles may be particles of any form suitable for carrying out the present disclosure, for example in bead or disk form, of asymmetrical geometric form, for example with one planar face, etc.

Any suitable size of magnetic or magnetizable particle may be used. The size may be selected for example as a function of the size of the microorganism and/or the size of the compartment containing the culture medium for carrying out the process of the disclosure and/or of the microorganism. The size may for example be a size substantially identical to the size of the biofilm-generating microorganism such that the at least two particles may be incorporated into a biofilm, for example formed by said microorganism, the aim being to use the magnetic or magnetizable particles as an inert equivalent of the microorganism. When these particles are mobile, the microorganisms of the same size may also move. When these particles are immobilized, the microorganisms of the same size cannot move either. Furthermore, particles of varied sizes may enable more detailed analysis of the structure of the biofilm: dimensions of the spaces within the structure, three-dimensional organization, stability of the adhesion to the surface, for example at the bottom of the tube or of the well of the microdilution plate in which the assay is carried out. Indeed, biofilms tend to become detached in shreds (scales) from their support as they age. In this case, a first phase is then observed of immobilization of the at least two particles during the growth of the biofilm. There is then a phase of degeneration of the biofilm with release of the at least two particles.

For example, the magnetic or magnetizable particles may have a size of for example 10 nm to 100 µm, for example from 0.1 to 10 µm (size of the most common microorganisms).

When the particles are incorporated in a biofilm, especially in the complex matrix generated by the growth of the microorganisms, composed of cell bodies, the adhesion systems of said microorganisms, for example filaments, pili, fimbriae, etc., more or less viscous substances, for example polysaccharides, alginates etc., secreted by said microorganisms, the application of the magnetic, or electric or electromagnetic field does not make it possible to cause movement of said particles incorporated in said biofilm.

When the particles are not incorporated in said biofilm, for example when the mobility of the particles is not hindered by the presence of bodies of microorganisms whose size is close to that of the particles, for example of the order of one to several micrometers, for example when the mobility of the particles is not hindered by the presence of the adhesion systems of said microorganisms, for example filaments, pili, fimbriae, etc., generating a tangle that blocks the progression of the particles, for example when the mobility of the particles is not hindered by the presence of more or less viscous substances secreted by said microorganisms, for example polysaccharides, alginates etc., for example when the mobility of the particles is not hindered by molecules associated with the growth of the biofilm of microorganisms, the application of the magnetic, electric or electromagnetic field causes the movement of said particles.

According to the disclosure, the process of the disclosure may be implemented with a plurality of particles, for example from 2 to 10 000 000, from 1000 to 1 000 000, from 10 000 to 1 000 000, from 100 000 to 1 000 000, from 10 000 to 100 000. The plurality of particles advantageously makes it possible to directly detect, without a complex visualization device and without stain, the interaction between said substances, unlike the processes of the prior art using a single particle and requiring complex visualization devices or stains to detect the interaction.

According to the disclosure, the particles may be illuminated, for example by means of a light source. The illumination advantageously makes it possible to enhance the contrast between the particles and the solution.

According to the disclosure, the observation may be carried out by any means known to those skilled in the art. This may for example be an optical device, for example a microscope, a camera, a document scanner, for example an EPSON Perfection V600 Photo scanner, or a visual observation.

According to the disclosure, the observation may make it possible to measure, for example, the intensity, the contrast, or the variance of the image, for example via any means known to those skilled in the art, for example imaging software, for example ImageJ, that makes it possible to measure, for example, differences in contrasts or intensities that correspond for example to the particles in zones from one image to another, and thereby to determine differences from one observation to another. This may for example be a comparison of the images obtained before and after applying mechanical, hydrodynamic or physical action, for example by carrying out a subtraction between images, for example by measuring the correlation coefficient between the images.

According to the disclosure, the use of particles that emit a signal, for example colored, excitable, fluorescent, phosphorescent, luminescent or radioactive particles, may for example allow an automated observation.

According to the disclosure, the conditions for carrying out the process of the disclosure, in particular for culturing the microorganism, are standardized culture conditions, for example pH, temperature, oxygenation, etc.

According to the disclosure, the inoculated culture media may be maintained at a temperature of from 10 to 45° C., preferably from 25° C. to 42° C., for example equal to 37° C.

According to the disclosure, the inoculated culture media may be maintained under a natural atmosphere, in a conventional incubator for example, or under a controlled atmosphere for microanaerophilic microorganisms or obligate anaerobes, according to any means known to those skilled in the art.

According to the disclosure, the field may be a magnetic, electric or electromagnetic field.

According to the disclosure, the magnetic field may be applied by any means known to those skilled in the art and/or suitable and/or commercially available means.

According to the disclosure, the magnetic, electric or electromagnetic field may be any field making it possible to move said at least two particles on said surface submerged in said solution, for example an electromagnetic field or a magnetic field. The magnetic, electric or electromagnetic field may be generated for example by a magnet or a solenoid. The magnet may for example be in the form of a bar, tip, or part, etc., or any suitable form for carrying out the present disclosure. The field may for example be applied by any means known to those skilled in the art, for example in pulses, by gradually increasing the electromagnetic field, by electromagnetic field variations or by a combination of these applications.

According to the disclosure, the process may also comprise a step e'), prior/subsequent to or replacing step e), for determining the biofilm formation index (BFI) value for each of the inoculated media and calculating the biofilm formation potential index per container (BPc) according to the following formula (I):

$$BPc = [1-(BFIe/BFIn)] \tag{I}$$

wherein BFIe corresponds to the biofilm formation index value in the inoculated medium and BFIn corresponds to the biofilm formation index value in a container which does not comprise microorganisms.

According to the disclosure, the BFIn value corresponds to the negative control.

In this embodiment, biofilm formation can be identified when the value of BPc is greater than a threshold value (S). According to the disclosure, the threshold value (S) may be calculated according to the following formula (II)

$$S = 1-[(mBFIn-3 \times stmBFIn)/2]/mBFIn \tag{II}$$

wherein mBFIn is equal to the mean of the BFIs of the negative controls, stmBFIn is equal to the calculated standard deviation of the mean of the BFIs of the negative controls.

According to the disclosure, the process may also comprise a step e'') subsequent to or simultaneously with the step e') for determining the threshold value (S) according to the following formula (II):

$$S = 1-[(mBFIn-3 \times stmBFIn)/2]/mBFIn \tag{II}$$

wherein mBFIn is equal to the mean of the BFIs of the negative controls, stmBFIn is equal to the calculated standard deviation of the mean of the BFIs of the negative controls.

Those skilled in the art, due to their general knowledge, will know how to calculate the mean of the BFIs of the negative controls and also the standard deviation of the mean.

In the present document, the process of the disclosure may comprise, for each measurement, at least three negative controls from which the mBFIn value and the stmBFIn value are calculated. For example, for each BPc calculation, the process may comprise at least three BFIn values from which the mean of the BFIs of the negative controls (mBFIn) and also the standard deviation of the mean (stmBFIn) may be calculated.

Those skilled in the art, due to their general knowledge, will know how to adapt the number of negative controls for the calculation of the mean of the BFIs of the negative controls (mBFIn) and also the standard deviation of the mean (stmBFIn) may be calculated.

According to the disclosure, when several negative controls are used to calculate the mBFIn value in formula (II), the BFIn value in formula (I) may be equal to the mBFIn value.

According to the disclosure, the inventors have surprisingly demonstrated that the biofilm-producing capacity may be determined as follows:
- a BPc value greater than or equal to the threshold value S from a concentration of microorganisms of from $1 \times 10^{-6}$ to $1 \times 10^{-4}$ McF corresponding to a strongly biofilm-producing microorganism,
- a BPc value greater than or equal to the threshold value S from a concentration of microorganisms of greater than $1 \times 10^{-4}$ and less than $1 \times 10^{-2}$ McF corresponding to a moderately biofilm-producing microorganism,
- a BPc value greater than or equal to the threshold value S from a concentration of microorganisms of $1 \times 10^{-2}$ McF corresponding to a weakly biofilm-producing microorganism,
- a BPc value less than the threshold value S, regardless of the concentration, corresponding to a non-biofilm-producing microorganism.

In the present document, the biofilm formation index (BFI) is obtained by analyzing the red-green-blue color components of the pixels of the image in order to determine the particle density per pixel, then by calculating the correlation between the particles to determine the particle aggregation density expressed by a BFI value. The BFI index is especially described in the document by Chavant et al. 2007 [5].

Figure 1:
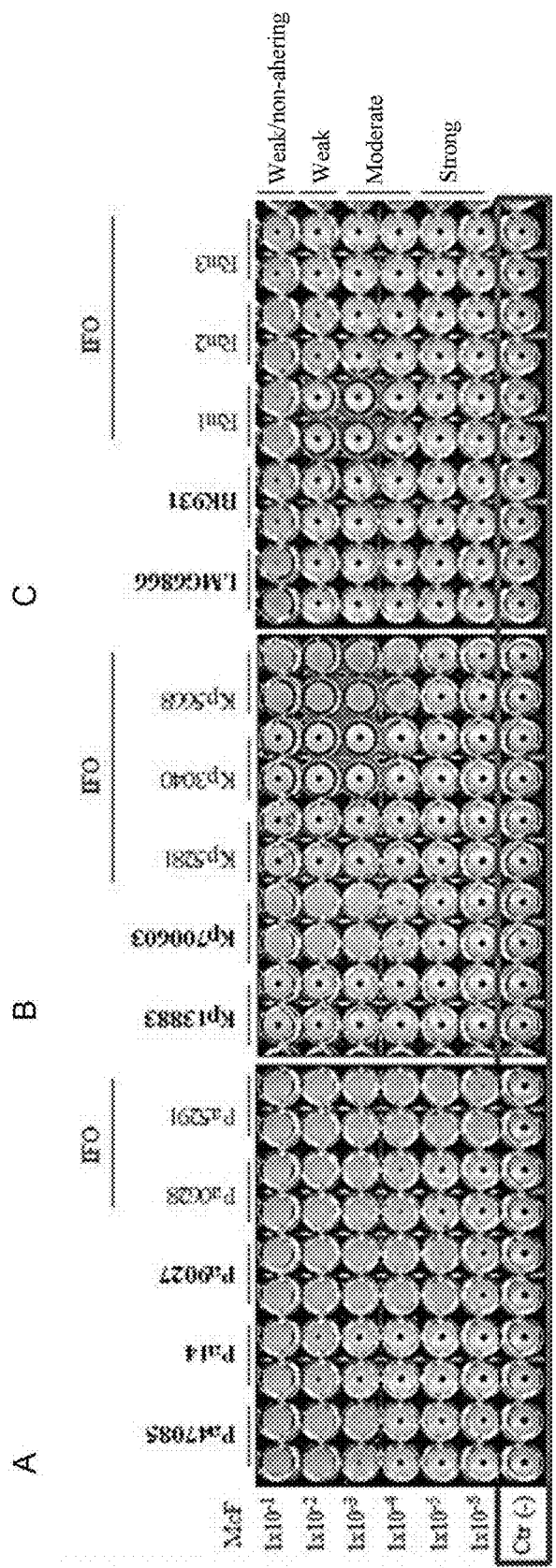
FIG. 1 is a photograph of a 96-well plate. It shows biofilm formation on 96-well polystyrene plates by Gram-negative bacteria: A) *P. aeruginosa* (Pa), B) *K. pneumoniae* (Kp) and C) *R. mannitolilytica*, isolated from the IFO hospital. The images were obtained after magnetization of the plates on the test block and digitization with the plate reader. The reference laboratory strains are indicated in bold. The absence of biofilm formation is revealed by the presence of the central black dot in the wells, corresponding to the coming together of the particles. The presence of biofilm is revealed by the absence of a black dot at the center of the wells. The wells corresponding to negative controls (Ctr (−)) containing solely BHI medium and the magnetic microparticles correspond to the bottom row of wells.

Other advantages may also become apparent to those skilled in the art on reading the examples below, illustrated by the appended figures and given by way of illustration.

EXAMPLES

Example 1: Evaluation of the Microorganism Biofilm-Producing Capacity

In the example below, an example of the process according to the disclosure is especially denoted characterization process or cBFRT process. In this example, the materials and methods used were the following:

Strains and Growth Conditions

Reference strain: *Staphylococcus aureus* American Type Culture Collection (ATCC) 25923, *Staphylococcus aureus* ATCC 6538, *Staphylococcus epidermidis* ATCC 14990, *Staphylococcus epidermidis* ATCC 12228, *Klebsiella pneumoniae* ATCC 700603, *Klebsiella pneumoniae* ATCC 13883, *Pseudomonas aeruginosa* ATCC 47085, *Pseudomonas aeruginosa* ATCC 9027, *Pseudomonas aeruginosa* PA14, *Ralstonia mannitolilytica* LMG 6866, *Ralstonia mannitolilytica* BK931 and the clinical isolates of bacteria were cultured aerobically on a nonselective agar (blood agar, chocolate agar, MacConkey agar) (Oxoid, Hampshire, United Kingdom) at 37° C.

Selection of the Isolates

A total of 52 clinical isolates collected from patients suffering from nosocomial infections, admitted to the IFO hospital in Rome, were evaluated. The bacteria were collected from different materials including chronic infections (ulcers), intravenous and urinary catheters, blood, urine, sputum and naso-bronchial lavage samples. An ulcer was classified as chronic if it had existed for at least 3 months (Dissemond, 2006). The study also comprised strains having an increased resistance to commonly used antibiotics, as determined according to the standard for antibiotic susceptibility tests by the VITEK2 system (bioMérieux, Florence, Italy). In particular, the strains of *P. aeruginosa* resistant to three or more classes of antibiotics were considered to be multidrug-resistant (MDR) microorganisms. The *K. pneumoniae* strains resistant to the majority of the beta-lactam antibiotics, including penicillins, cephalosporins, and aztreonam monobactam, growing on selective chromogenic medium chromID ESBL (bioMérieux, Florence, Italy) were classified as having extended-spectrum beta-lactamase (ESBL). The phenotypic detection of ESBL producers was further defined using the disk test (Oxoid, United Kingdom), as described in De Gheldre, 2003; Moremi, 2014. The *K. pneumoniae* strains resistant to carbapenems and identified by a selective chromogenic medium chromID CARBA (bioMérieux, Florence, Italy) are referenced as *K. pneumoniae* carbapenemase (KPC)-producing. The methicillin-resistant *Staphylococcus aureus* (MRSA) were penicillin binding protein (PBP)-producing after confirmation by the PBP2' latex agglutination test kit (Oxoid Ltd, Basingstoke, United Kingdom). The vancomycin-resistant enterococci (VRE) were identified by susceptibility tests and confirmed by selective chromogenic media chromID VRE (bioMérieux, Florence, Italy). The levels of susceptibility to antibiotics were compared with those defined by the minimum inhibitory concentration (MIC) according to the interpretation criteria recommended by the European Committee on Antimicrobial Susceptibility Testing (EUCAST). The number of species and the characteristics of the strains tested are given in table 2. The isolates were stored at −70° C. in Cryobank tubes (Copan Italia SpA) and cultured overnight at 37° C. on a specific agar dish before the test.

Preparation of the Inoculum

The biofilm formation was evaluated by the BioFilm Ring Test (BFRT) (BioFilm Control, Saint-Beauzire, France), using the commercially available kit (BioFilm Control, Saint Beauzire, France). The toner solution (TON004) containing magnetic beads was mixed in a brain heart infusion medium (BHI, Difco, Detroit, Mich., USA) according to the manufacturer's instructions. In order to determine the biofilm-producing capacity/classification of the microorganisms, the inoculum was prepared as follows. A fresh culture of bacteria on agar, cultured overnight, was used for each strain to be tested. The cultured bacteria were then transferred by a sterile inoculation loop into a sterile tube containing 2 ml of 0.45% saline solution, at the equivalent to 1.0±0.3 McFarland turbidity standard (McF) and mixed thoroughly. Subsequently, 200 µl of the inoculum were transferred into the wells of a 96-well polystyrene plate. From this initial inoculum, serial dilutions by a factor of 10 were performed, from $1\times10^{-1}$ to $1\times10^{-6}$ McF, by transferring 20 µl of the microbial solution in 200 µl of the BHI/TON mixture.

One or more laboratory strains were included in each plate as standard reference and quality control. One well containing the BHI/TON mix without microbial cells was used as negative control in each experiment.

After five hours of incubation at 37° C. without stirring (static culture), the wells were covered with a few drops of contrast liquid (inert opaque oil used for the reading step, included in the BFRT kit), placed for 1 min on the block carrying 96 mini magnets (test block) and scanned with a specially designed plate reader (BIOFILM pack, BioFilm Control, Saint Beauzire, France). The adhesion strength of each strain was expressed as biofilm formation index (BFI), which was calculated by specialized software initially described in Chavant, 2007. The BFI values were used to measure the biofilm formation potential (BP), using the formula:

$$BPc=[1-(BFIe/BFIn)] \qquad (I)$$

wherein BFIe corresponds to the biofilm formation index value in the inoculated medium and BFIn corresponds to the biofilm formation index value in a container which does not comprise microorganisms.

The threshold value (S) was calculated according to the following formula (II)

$$S=1-[(mBFIn-3\times stmBFIn)/2]/mBFIn \qquad (II)$$

wherein mBFIn is equal to the mean of the BFIs of the negative controls, stmBFIn is equal to the calculated standard deviation of the mean of the BFIs of the negative controls.

In this example, the BFIn values were from 18 to 20. The calculated value of S was equal to 0.53.

BPc values above the calculated S value were considered as biofilm-producing. Thus, the final dilution for which the value is above the calculated S value made it possible to identify the biofilm-forming capacity of the microorganism. Consequently, the microorganisms were classified in the following categories: non-adhering cells, weakly biofilm-producing, moderately biofilm-producing and strongly biofilm-producing. Each microbial culture was analyzed in duplicate, and the experiments were repeated at least 3 times for each strain in order to evaluate the reproducibility, accuracy and precision of the measurement. The values were considered to be valid if the standard deviation between the duplicates was less than 8%. The replicas showed complete agreement in the classification/categorization of the microorganisms.

Evaluation of Biofilm Formation with the Crystal Violet Assay 96-well polystyrene plates were inoculated with 200 µl of an initial bacterial suspension ($10^5$ CFU/ml) in BHI medium and incubated at 37° C. for 24 and 48 hours without stirring. Each condition was carried out in triplicate. The medium was removed from the wells, which were washed 3 times with 200 µl of sterile distilled water. The plates were air-dried for 45 minutes and the adhering cells were stained with 200 µl of 0.1% crystal violet solution. After 20 minutes, the stain was eliminated and the wells were washed four times with 300 µl of sterile distilled water to eliminate the excess stain. The stain incorporated by the biofilm-forming cells was dissolved with 200 µl of an 80/20% ethanol/acetone mixture and the absorbance of each well was measured by spectrophotometry at 570 nm ($OD_{570}$) using the automated PhD Ix™ system (Bio-Rad Laboratories, Hercules, Calif., USA).

For the comparative analysis, $OD_{570}$ values were use to semi-quantitatively classify the biofilm production for the bacterial strains, according to the process described in Stepanovic et al (Stepanovic, 2000). Briefly, the threshold optical density (ODc) was defined as three standard deviations above the mean optical density (OD) of the negative control. Thus, the strains were classified as follows: OD<ODc=non-adhering; ODc<OD<2×ODc=weakly biofilm-producing; 2×ODc<OD<4×ODc=moderately biofilm-producing; and OD>4×ODc=strongly biofilm-producing.

All the assays were carried out in triplicate, with reference strains and clinical isolates tested three times over to evaluate any potential variations in the conditions for assaying the biofilm.

Statistical Methods

The kappa coefficient test was used to determine the agreement between the results obtained with the characterization process and crystal violet (CV). The agreement was calculated according to Viera (Viera, 2005): kappa=0.81-1, very good; kappa=from 0.61 to 0.80, good; kappa 0.41 to 0.60, moderate; kappa=0.21 to 0.40, fair; kappa≤0.20, poor. The results of biofilm formation obtained with the two methods were compared also using McNemar's test. Values of p<0.05 were considered to be significant.

Results and Discussion

Standardization of the Bacterial Inoculums to McFarland Standards

Given that different microorganisms, including mucoid or non-mucoid strains, or other characteristics such as the size, can affect the measurement of initial cellular concentration and consequently the reliability of the assay, the precision of the initial inoculum was measured with a densitometer and verified by counting the colony forming units (CFUs) (Welch, 2012).

The data reported in table 1 showed that one McF unit varied from $0.6 \times 10^9$ CFU/ml for *R. mannitolilytica* to $1.4 \times 10^9$ CFU/ml for *P. aeruginosa*. This result demonstrates that measuring the initial inoculum with the densitometer does not generate significant differences. The mean value of the CFU/ml for the different bacterial strains from 1 McF corresponds to $1.0 \times 10^9 \pm 3.6 \times 10^8$, which is in the same range of values as indicated previously for bacteria (Eng et al, 1984). Consequently, the CFU values show that the McF standard is highly reproducible, independently of the bacterial species or microbial phenotypes, ensuring the precision of the assay at the moment of the inoculum.

TABLE 1

CFU/ml correspondence to 1 McFarland for the bacteria used to inoculate the cBFRT assay. The values represent the mean CFU/ml ± SD of two repetitions.

| Microbial strain | CFU/ml |
|---|---|
| *P. aeruginosa* | $1.4 \times 10^9 \pm 7.2 \times 10^8$ |
| *K. pneumoniae* | $0.9 \times 10^9 \pm 7.9 \times 10^8$ |
| *R. mannitolilytica* | $0.6 \times 10^9 \pm 2.6 \times 10^8$ |
| *S. aureus* | $1.3 \times 10^9 \pm 8.4 \times 10^8$ |
| *S. epidermidis* | $1.1 \times 10^9 \pm 7.1 \times 10^8$ |
| Other Gram+ | $1.1 \times 10^9 \pm 8.7 \times 10^8$ |
| Mean | $1.0 \times 10^9 \pm 3.2 \times 10^8$ |

Evaluation of Biofilm Production in Gram-Negative and Gram-Positive Bacteria

The biofilm-forming ability was initially evaluated on isolates of *P. aeruginosa*, which is a Gram-negative opportunistic pathogen with a noteworthy biofilm-forming capacity, which ensures its persistence in the environment and in chronic infectious diseases (Høiby et al, 2010).

Among the 12 strains tested, three were laboratory strains with a known biofilm-forming capacity. These comprised, respectively, Pa47085 (moderate capacity) (Schaber, 2004), PA14 (weak capacity) (Rahme, 1995), and Pa9027 (strong capacity), (Stapleton, 1993), while the 9 remaining strains of *P. aeruginosa* were clinical isolates collected from hospitalized patients (table 2).

TABLE 2

Characteristics of the clinical isolates used in this study. Multidrug-resistant (MDR), having extended-spectrum beta-lactamase (ESBL), *K. pneumoniae* carbapenemase (KPC)-producing, methicillin-resistant *S. aureus* (MRSA), vancomycin-resistant *enterococci* (VRE). Catheter-associated urinary tract infections (CA-UTI), central venous catheter (CVC), catheter-associated blood infection (CA-BI).

| Bacterial species | Clinical isolates | Phenotype | Site of isolation |
|---|---|---|---|
| Gram-negative bacteria | | | |
| *P. aeruginosa* | 9 | MDR (2) | CA-BI (2) |
| | | MDR (1) | Chronic ulcer (2) |
| | | — | Wound (1) |
| | | — | Urine (1) |
| | | — | Respiratory (3) |
| *K. pneumoniae* | 8 | KPC (1) | CVC (1) |
| | | — | Blood (2) |
| | | — | Wound (1) |
| | | ESBL (1) | CA-UTI (2) |
| | | — | Respiratory (2) |
| *R. mannitolilytica* | 8 | — | Blood (8) |
| Gram-positive bacteria | | | |
| *S. aureus* | 10 | MRSA (1) | CVC (1) |
| | | MRSA (3) | Chronic ulcer (6) |
| | | — | Skin (2) |
| | | — | Respiratory (1) |
| *S. epidermidis* | 8 | — | Blood (6) |
| | | — | Wound (2) |
| Other Gram+ | 9 | — | Blood (2) |
| | | VRE (1) | Wound (6) |
| | | — | Urine (1) |
| Gram-negative bacteria | | | |
| *P. aeruginosa* | 9 | MDR (2) | CA-BI (2) |
| | | MDR (1) | Chronic ulcer (2) |
| | | — | Wound (1) |
| | | — | Urine (1) |
| | | — | Respiratory (3) |
| *K. pneumoniae* | 8 | KPC (1) | CVC (1) |
| | | — | Blood (2) |
| | | — | Wound (1) |
| | | ESBL (1) | CA-UTI (2) |
| | | — | Respiratory (2) |
| *R. mannitolilytica* | 8 | — | Blood (8) |
| Gram-positive bacteria | | | |
| *S. aureus* | 10 | MRSA (1) | CVC (1) |
| | | MRSA (3) | Chronic ulcer (6) |
| | | — | Skin (2) |
| | | — | Respiratory (1) |
| *S. epidermidis* | 8 | — | Blood (6) |
| | | — | Wound (2) |
| Other Gram+ | 9 | — | Blood (2) |
| | | VRE (1) | Wound (6) |
| | | — | Urine (1) |

After five hours of incubation, the reference strain PA14 immobilized the magnetic beads only at the highest concentration of cells (McF=$1 \times 10^{-2}$), which suggests a weak capacity for adhesion and qualifies it as weakly biofilm-producing (FIG. 1). Similarly, PA14 was classified as weakly biofilm-producing (table 3A). Pa47085 adheres more readily to the surface of the wells and blocks the magnetic beads at a concentration of McF=$1 \times 10^{-3}$, thereby identifying this strain as moderately biofilm-producing. Similarly, Pa9027 was confirmed as being strongly biofilm-producing at a cellular concentration of McF=$1 \times 10^{-6}$. These results are in agreement with those described previously for these laboratory strains (Schaber, 2004; Rahme, 1995; Stapleton, 1993).

Among the clinical isolates, six strains proved to be strongly biofilm-producing. In particular, this includes the three MDR strains, including two originating from patients suffering from catheter-associated blood infections (Pa6020-IFO, Pa5252-IFO), chronic ulcers (Pa5797-IFO), and the strains isolated from bronchioalveolar lavage from a patient suffering from cystic fibrosis (Pa0629-IFO), from pleural fluid (Pa5291-IFO) and originating from a patient with an infected wound (Pa0118-IFO). Two strains were classified as moderately biofilm-producing, deriving from a patient suffering from a chronic ulcer (Pa3019-IFO) and from another bronchoalveolar lavage from a patient suffering from cystic fibrosis (Pa0628-IFO). Conversely, the only physiological environments, which may contribute to explaining the difficulty in eradicating these infections once they are established in solid tissues (Sanchez, 2013). Another important observation emerging from the limited number of clinical isolates analyzed was the relatively high incidence of non-adhering strains. More precisely, we observed that only 50% of the *K. pneumoniae* included in this study were capable of producing biofilm. This value is in agreement with previous in vitro studies which demonstrate that only 40% of *K. pneumoniae* isolated from different materials were able to produce biofilm (Yang, 2008).

TABLE 3

Analysis of the plates obtained with the characterization process for A) *P. aeruginosa*, B) *K. pneumoniae* and C) *R. mannitolilytica*.

| A) McF | Pa47085 | Pa14 | Pa9027 | Pa6020-IFO | Pa0115-IFO | Pa3019-IFO | Pa5797-IFO | Pa0628-IFO | Pa0629-IFO | Pa5252-IFO | Pa0118-IFO | Pa5291-IFO | |
|---|---|---|---|---|---|---|---|---|---|---|---|---|---|
| $1 \times 10^{-1}$ | 0.97 | 0.98 | 0.99 | 0.98 | 0.90 | 0.97 | 0.99 | 1.00 | 1.00 | 0.97 | 0.98 | 1.00 | Non-adhering/weak |
| $1 \times 10^{-2}$ | 0.97 | 0.72 | 0.99 | 0.96 | 0.33 | 0.99 | 1.00 | 1.00 | 1.00 | 0.95 | 0.97 | 1.00 | Weak |
| $1 \times 10^{-3}$ | 0.96 | 0.01 | 0.95 | 0.92 | 0.12 | 0.98 | 0.99 | 0.98 | 0.98 | 0.98 | 0.93 | 1.00 | Moderate |
| $1 \times 10^{-4}$ | 0.01 | −0.02 | 0.97 | 0.74 | 0.06 | 0.64 | 0.87 | 0.58 | 0.96 | 0.96 | 0.89 | 1.00 | Moderate |
| $1 \times 10^{-5}$ | 0.03 | 0.03 | 0.96 | 0.57 | 0.07 | −0.02 | 0.53 | 0.07 | 0.87 | 0.92 | 0.78 | 1.00 | Strong |
| $1 \times 10^{-6}$ | 0.05 | 0.05 | 0.52 | 0.39 | 0.08 | 0.00 | 0.49 | −0.01 | 0.71 | 0.87 | 0.56 | 0.93 | Strong |
| | 1 | 2 | 3 | 4 | 5 | 6 | 7 | 8 | 9 | 10 | 11 | 12 | |

| B) McF | Kp13883 | Kp700603 | Kp5553-IFO | Kp5776-IFO | Kp5668-IFO | Kp5281-IFO | Kp3040-IFO | Kp0068-IFO | Kp5656-IFO | Kp5783-IFO | |
|---|---|---|---|---|---|---|---|---|---|---|---|
| $1 \times 10^{-1}$ | 0.07 | 0.98 | 0.92 | 0.86 | 1.00 | 0.01 | 0.04 | 1.00 | −0.01 | 0.15 | Non-adhering/weak |
| $1 \times 10^{-2}$ | 0.08 | 0.94 | 0.91 | 0.81 | 0.94 | 0.01 | 0.04 | 1.00 | 0.00 | 0.05 | Weak |
| $1 \times 10^{-3}$ | 0.03 | 0.82 | 0.84 | 0.76 | 0.95 | −0.02 | 0.04 | 0.99 | −0.01 | 0.00 | Moderate |
| $1 \times 10^{-4}$ | 0.07 | 0.22 | 0.37 | 0.26 | 0.92 | 0.01 | 0.06 | 0.75 | 0.04 | 0.02 | Moderate |
| $1 \times 10^{-5}$ | −0.01 | −0.03 | 0.05 | 0.00 | 0.25 | 0.02 | 0.00 | 0.01 | 0.04 | −0.01 | Strong |
| $1 \times 10^{-6}$ | 0.00 | 0.02 | 0.02 | 0.02 | 0.11 | 0.04 | 0.01 | −0.05 | 0.03 | 0.01 | Strong |
| | 1 | 2 | 3 | 4 | 5 | 6 | 7 | 8 | 9 | 10 | |

| C) McF | LMG 6866 | BK931 | Rm1-IFO | Rm2-IFO | Rm3-IFO | Rm4-IFO | Rm5-IFO | Rm6-IFO | Rm7-IFO | Rm8-IFO | |
|---|---|---|---|---|---|---|---|---|---|---|---|
| $1 \times 10^{-1}$ | 0.88 | 0.66 | 0.88 | 0.99 | 0.59 | 0.57 | 0.91 | 0.51 | 0.57 | 0.94 | Non-adhering/weak |
| $1 \times 10^{-2}$ | 0.26 | 0.14 | 0.17 | 0.61 | 0.13 | 0.11 | 0.16 | 0.12 | 0.15 | 0.54 | Weak |
| $1 \times 10^{-3}$ | 0.09 | 0.03 | 0.10 | 0.13 | 0.05 | 0.07 | 0.07 | 0.10 | 0.09 | 0.15 | Moderate |
| $1 \times 10^{-4}$ | 0.00 | 0.04 | 0.07 | 0.01 | 0.11 | 0.12 | 0.02 | 0.10 | 0.10 | 0.04 | Moderate |
| $1 \times 10^{-5}$ | 0.02 | 0.06 | 0.06 | 0.10 | 0.09 | 0.12 | 0.02 | 0.09 | 0.10 | 0.10 | Strong |
| $1 \times 10^{-6}$ | 0.03 | 0.10 | 0.05 | 0.03 | 0.09 | 0.13 | 0.01 | 0.09 | 0.11 | 0.09 | Strong |
| | 1 | 2 | 3 | 4 | 5 | 6 | 7 | 8 | 9 | 10 | | weakly biofilm-producing strain was a mucoid strain isolated from a urinary infection (Pa0115-IFO).

The assay was then use to evaluate the biofilm-forming capacity of *Klebsiella pneumoniae*, one of the most significant nosocomial pathogens (Podschun, 1998). The results, summarized in FIG. 1B and in table 3B, show that the reference strains Kp700603 and Kp13883 were, respectively, non-adhering/biofilm producing and moderately biofilm-producing, confirming previous reports (Naparstek, 2014). Regarding the clinical strains Kp0068-IFO (urinary infection), Kp5553-IFO (an ESBL strain from a urinary sound), Kp5668-IFO (a KPC strain from a central venous catheter) and Kp5776-IFO (from pleural fluid), they were found to be moderately biofilm-producing. Conversely, the strains isolated from blood cultures (Kp5656-IFO, Kp5281-IFO, Kp5783-IFO, Kp3040-IFO) but not originating from catheter-associated bacterial blood infections, exhibited a mucoid phenotype and were deemed to be non-adhering and non-biofilm-producing, This data is in agreement with previous reports indicating a higher frequency of biofilm-forming strains in *K. pneumoniae* isolated from non-fluid In the table above, the bacteria were classified as a function of the BP value, also referred to as BPc, measured. The cut-off/threshold was established at 0.53. A value of between 1 and 0.53 corresponds to biofilm formation, a value of less than 0.53 to a possible absence of biofilm, or a non-significant biofilm formation.

*R. mannitolilytica* is rarely isolated from clinical samples and represents the most widespread species of the genus *Ralstonia* found in patients suffering from cystic fibrosis (Coenye, 2005). *R. mannitolilytica* has been associated with epidemics around the world (Ryan, 2014) and the hypothesis of the biofilm-forming capacity of this bacterium has been raised numerous times as a strategy for survival in difficult environments and in clinical settings, although it has rarely been tested. The present strains analyzed were isogenic clinical isolates from an epidemic occurring in the oncology department in the IFO hospital in 2014. Two reference strains, *R. mannitolilytica* LMG 6866 (De Baere, 2001) and *R. mannitolilytica* BK931 (Marroni, 2003), were evaluated in comparison, although their biofilm-producing capacity is unknown. The results from FIG. 10 and table 3C revealed that the reference strains LMG 6866 and BK931 were weakly biofilm-producing. Similarly, the 8 strains of *R. mannitolilytica*, isolated from blood culture, were weakly biofilm-producing/non-adhering.

Figure 2:
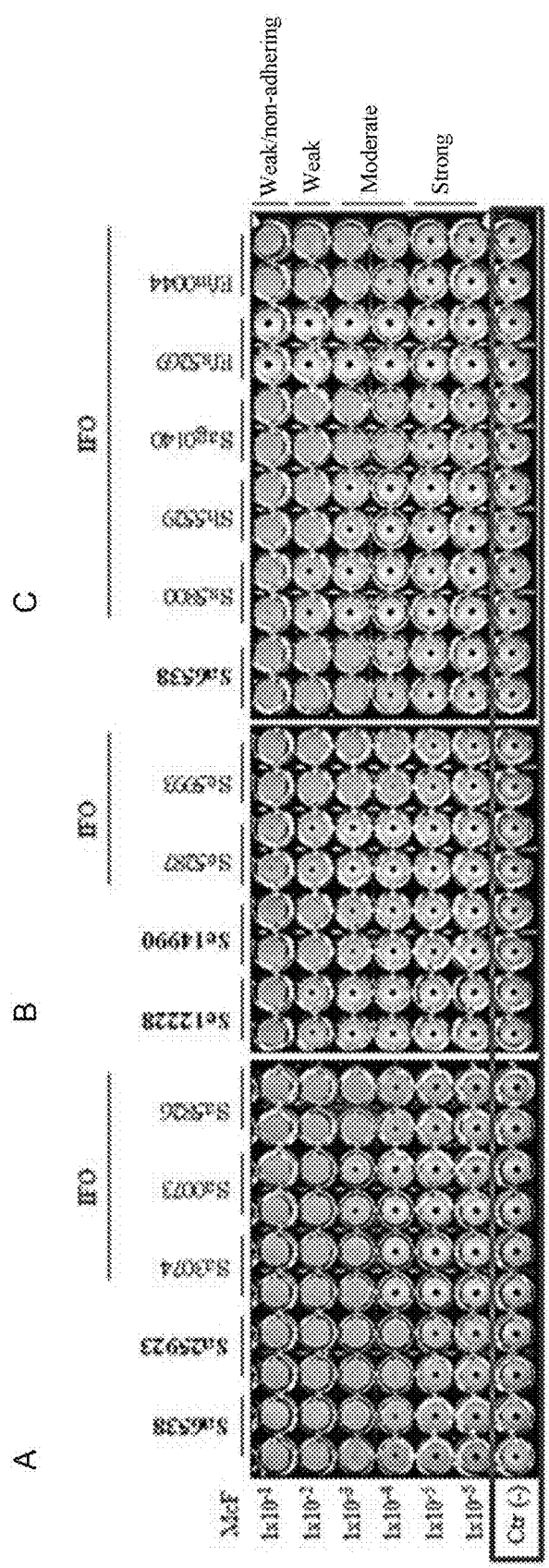
FIG. 2 is a photograph of a 96-well plate. It shows biofilm formation on 96-well polystyrene plates for Gram-positive bacteria: A) *S. aureus* (SA), B) *S. epidermidis* (SE) and C) different Gram-positive bacteria isolated at the IFO hospital. The images were obtained after magnetization of the plates on the test block and digitization with a plate reader. The reference laboratory strains are indicated in bold. The absence of biofilm formation is revealed by the presence of the central black dot in the wells, corresponding to the coming together of the particles. The presence of biofilm is revealed by the absence of a black dot at the center of the wells. The wells corresponding to negative controls (Ctr (−)) containing solely BHI medium and the magnetic microparticles are outlined in red.

Subsequently, the biofilm-forming ability was studied for different Gram-positive bacteria. More precisely, strains of *Staphylococcus aureus*, which have been associated with different types of human infections, comprising skin infections, endocarditis, bone infections, septic shock and biofilm-associated chronic infections (Otto, 2008) were evaluated. The reference strains Sa6538 and Sa25923, known to form biofilms (Latimer, 2012; Croes, 2009), were confirmed as strongly biofilm-producing and moderately biofilm-producing (FIG. 2A and table 4a). Among the clinical isolates, five strains were deemed to be moderately biofilm-producing (Sa3074-IFO, Sa3050-IFO, Sa0186-IFO, Sa5674-IFO and Sa5826-IFO) and three strains isolated from patients suffering from chronic ulcers were classified as strongly biofilm-producing (Sa3146-IFO, Sa3079-IFO and Sa3065-IFO). Among the four MRSA strains, two were moderately biofilm-producing (Sa0186-IFO, Sa5826-IFO) and two were strongly biofilm-producing (Sa3146-IFO and Sa3065-IFO). The only two weakly biofilm-producing strains originated such as a probe or an implanted device (Otto, 2009). While *S. epidermidis* has a weak pathogenic potential, it has been isolated in 40% of bacterial blood infections (Suetens, 2007). This high occurrence probably originates from the fact that it is a ubiquitous colonizer of human skin, and consequently is a possible source of contamination for devices when they are inserted or removed (Otto, 2009). Nonetheless, the biofilm-forming capacity of *S. epidermidis* is considered to be the most relevant determinant of its virulence (O'Gara, 2001; Götz, 2002; Cerca, 2005). In our assays, the reference strains Se12228 (Zhang, 2003) and Se14990 (Stepanovic, 2003) were classified, respectively, as weakly biofilm-producing and moderately biofilm-producing (FIG. 2B and table 4B). These results are in agreement with the data available in the literature. The analysis of the adhesion capacity by the assay revealed that 5 of the 6 clinical isolates derived from blood cultures (Se5287-IFO, Se5669-IFO, Se5934-IFO, Se5752-IFO and Se5845-IFO), were weakly biofilm-producing. One strain isolated from a catheter-associated blood infection (Se5993-IFO) proved to be moderately biofilm-producing. The two other strains of *S. epidermis*, isolated from wounds, were both classified as moderately biofilm-producing.

TABLE 4 analysis of the plates obtained with the process A) *S. aureus* B) *S. epidermidis* and C) various Gram-positive bacteria.

| A) McF | Sa6538 | Sa25923 | Sa3074-IFO | Sa3032-IFO | Sa3050-IFO | Sa0073-IFO | Sa0186-IFO | Sa5674-IFO | Sa5826-IFO | Sa3146-IFO | Sa3079-IFO | Sa3065-IFO | |
|---|---|---|---|---|---|---|---|---|---|---|---|---|---|
| $1 \times 10^{-1}$ | 1.00 | 1.00 | 1.00 | 1.00 | 1.00 | 1.00 | 1.00 | 1.00 | 1.00 | 1.00 | 1.00 | 1.00 | Non-adhering/weak |
| $1 \times 10^{-2}$ | 0.99 | 0.99 | 0.98 | 0.99 | 0.94 | 1.00 | 1.00 | 0.99 | 0.99 | 0.98 | 0.99 | 0.99 | Weak |
| $1 \times 10^{-3}$ | 0.95 | 0.99 | 0.92 | 0.09 | 0.84 | 0.44 | 0.98 | 0.99 | 0.98 | 0.98 | 0.99 | 0.97 | Moderate |
| $1 \times 10^{-4}$ | 0.05 | 0.94 | 0.11 | 0.10 | 0.08 | 0.04 | 0.56 | 0.45 | 0.33 | 0.98 | 0.97 | 0.98 | Moderate |
| $1 \times 10^{-5}$ | 0.09 | 0.54 | 0.12 | 0.03 | 0.10 | 0.04 | 0.05 | 0.02 | 0.02 | 0.93 | 0.74 | 0.99 | Strong |
| $1 \times 10^{-6}$ | 0.03 | 0.01 | 0.03 | 0.04 | 0.05 | 0.03 | 0.00 | 0.03 | −0.01 | 0.70 | 0.64 | 0.80 | Strong |
| | 1 | 2 | 3 | 4 | 5 | 6 | 7 | 8 | 9 | 10 | 11 | 12 | |

| B) McF | Se12228 | Se14990 | Se5287-IFO | Se5669-IFO | Se5899-IFO | Se1501-IFO | Se5934-IFO | Se5752-IFO | Se5845-IFO | Se5993-IFO | |
|---|---|---|---|---|---|---|---|---|---|---|---|
| $1 \times 10^{-1}$ | 0.99 | 1.00 | 0.94 | 0.97 | 0.99 | 0.98 | 0.97 | 0.99 | 0.99 | 1.00 | Non-adhering/weak |
| $1 \times 10^{-2}$ | 0.59 | 0.99 | 0.62 | 0.98 | 0.99 | 0.91 | 0.84 | 0.99 | 0.99 | 0.98 | Weak |
| $1 \times 10^{-3}$ | 0.29 | 0.81 | 0.27 | 0.28 | 0.64 | 0.53 | 0.45 | 0.46 | 0.34 | 0.98 | Moderate |
| $1 \times 10^{-4}$ | 0.20 | 0.27 | 0.20 | 0.00 | 0.05 | 0.20 | 0.16 | 0.12 | 0.05 | 0.87 | Moderate |
| $1 \times 10^{-5}$ | 0.13 | 0.28 | 0.13 | 0.01 | 0.03 | 0.02 | 0.03 | 0.01 | 0.02 | 0.44 | Strong |
| $1 \times 10^{-6}$ | 0.01 | 0.02 | 0.03 | 0.06 | 0.02 | 0.02 | 0.05 | 0.03 | 0.05 | 0.01 | Strong |
| | 1 | 2 | 3 | 4 | 5 | 6 | 7 | 8 | 9 | 10 | |

| C) McF | Sa6538 | Ss5800-IFO | Sh5529-IFO | Sh5592-IFO | Sag0140-IFO | Sag0093-IFO | Efm5304-IFO | Efm5515-IFO | Efs0044-IFO | Efs5269-IFO | |
|---|---|---|---|---|---|---|---|---|---|---|---|
| $1 \times 10^{-1}$ | 1.00 | 0.87 | 0.96 | 1.00 | 0.93 | 1.00 | 0.62 | 0.94 | 0.98 | 0.07 | Non-adhering/weak |
| $1 \times 10^{-2}$ | 0.99 | 0.21 | 0.83 | 0.90 | 0.97 | 1.00 | 0.48 | 0.83 | 0.97 | 0.06 | Weak |
| $1 \times 10^{-3}$ | 0.94 | 0.13 | 0.35 | 0.64 | 0.91 | 0.95 | 0.12 | 0.62 | 0.95 | 0.07 | Moderate |
| $1 \times 10^{-4}$ | 0.06 | −0.06 | 0.07 | 0.12 | 0.87 | 0.81 | −0.02 | 0.15 | 0.39 | 0.05 | Moderate |
| $1 \times 10^{-5}$ | 0.04 | 0.14 | 0.06 | 0.01 | 0.22 | 0.63 | −0.03 | 0.05 | −0.04 | 0.05 | Strong |
| $1 \times 10^{-6}$ | 0.01 | 0.04 | 0.04 | 0.03 | 0.24 | 0.52 | 0.00 | 0.06 | 0.03 | 0.06 | Strong |
| | 1 | 2 | 3 | 4 | 5 | 6 | 7 | 8 | 9 | 10 | | from children suffering from mild atopic dermatitis (Sa3032-IFO and Sa0073-IFO). None of the strains analyzed was classified as non-adhering or non-producing. This result is in agreement with previous reports describing the effectiveness of *S. aureus* in producing biofilm (Otto, 2008; Periasamy, 2012).

*Staphylococcus epidermidis*, a major component of the normal microbial population of human skin, is a significant nosocomial pathogen in patients with predisposing factors Other Gram-positive bacteria, recognized as significant nosocomial pathogens, were analyzed. The *S. aureus* strain Sa6538 was used as reference strain and the bacteria analyzed included: *Staphylococcus haemolyticus, Streptococcus sanguinis, Streptococcus agalactiae, Enterococcus faecium* and *Enterococcus faecalis*. More precisely, the strains of *S. agalactiae* (Sag0140-IFO and Sag0093-IFO) isolated from infected ulcers were found to be moderately/strongly biofilm-producing (FIG. 2C and table 4C). *E. faecium*

Figure 3:
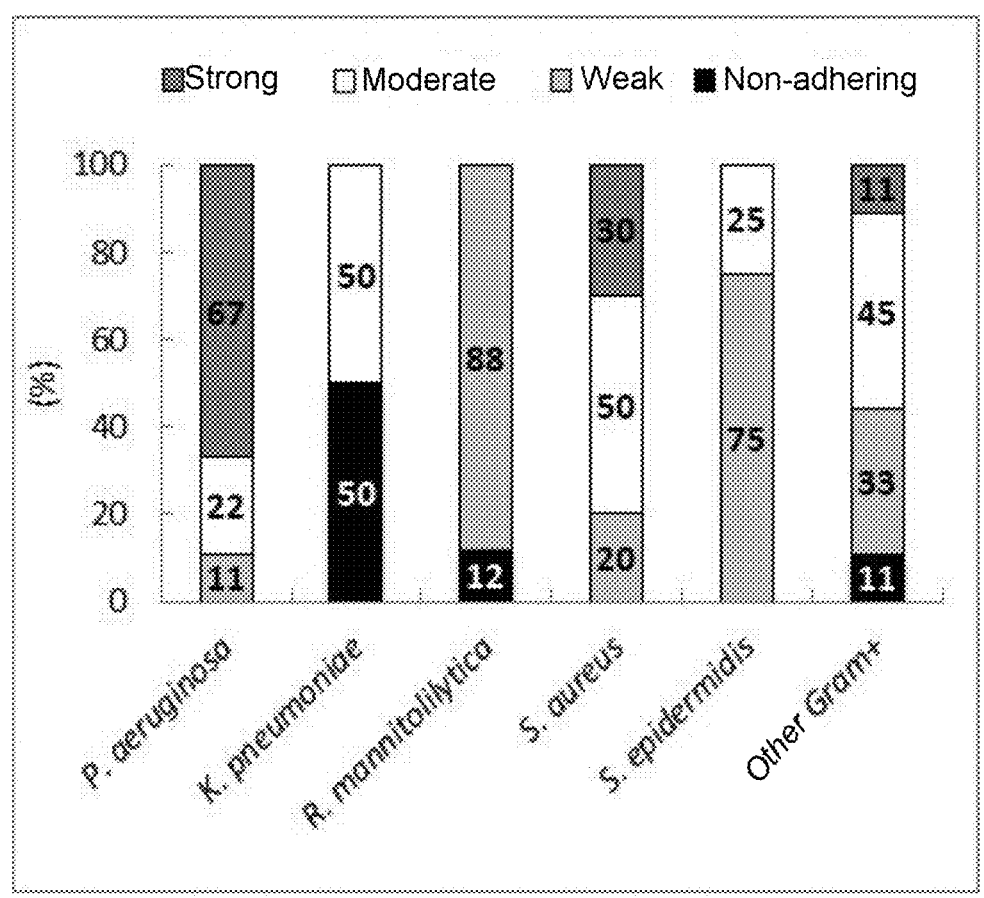
FIG. 3 is a bar chart representing the percentage of clinical isolates of each species, classified as a function of their biofilm-producing capacity measured by the process, namely strongly producing (dark gray zone), moderately producing (white zone), weakly producing (light gray zone) and non-producing/non-adhering (black zone).
Figure 4:
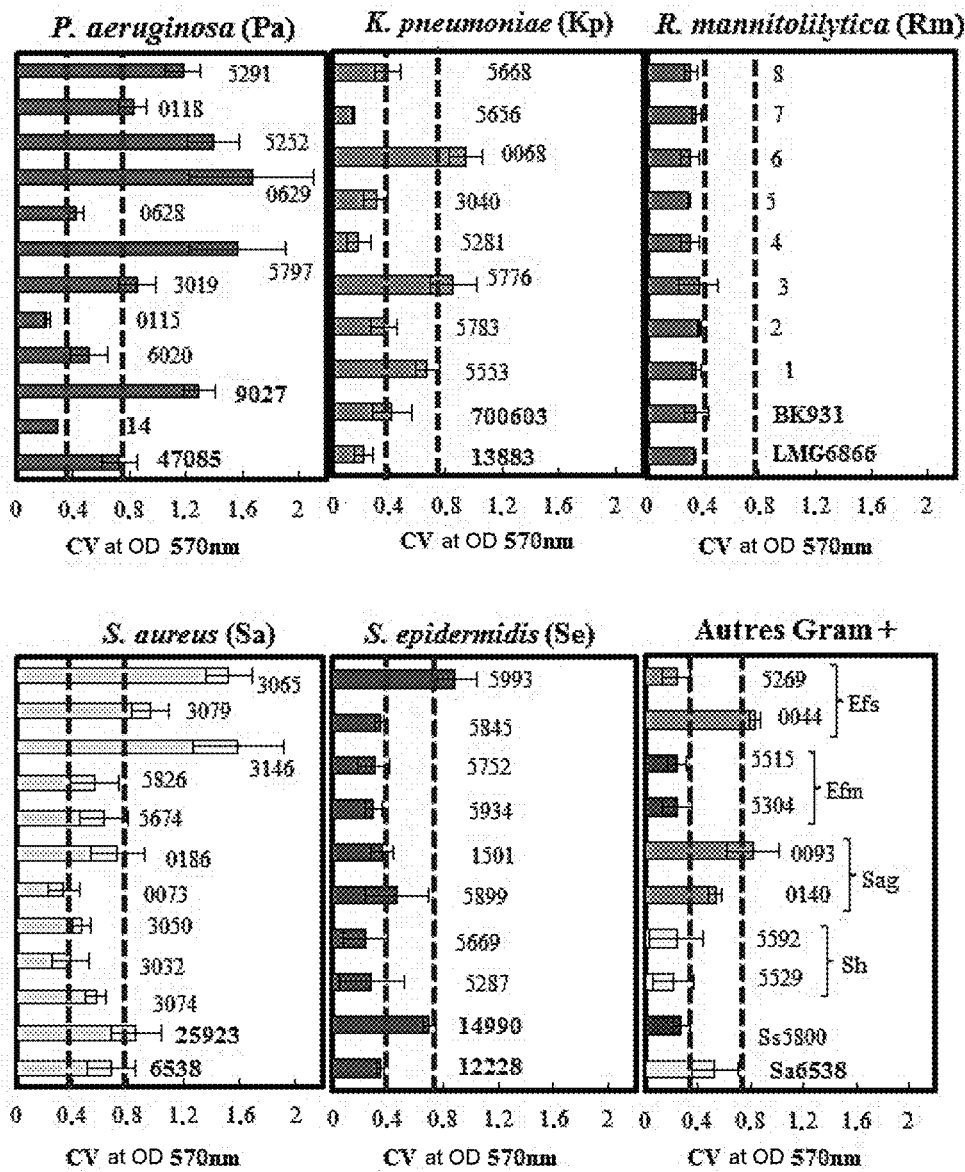
FIG. 4 is a bar chart representing the results of the quantitative analysis of biofilm formation by crystal violet (CV) staining of clinical isolates of *P. aeruginosa, K. pneumoniae, R. mannitolilytica, S. aureus, S epidermidis* and other Gram-positive bacteria. The isolates were classified as a function of their threshold values during optical density (OD) measurements, at a wavelength of 570 nm (OD570), of the medium. When the OD570 value is <0.18, the isolates are non-producing/non-adhering, when the OD570 is between 0.18 and 0.37 they are weakly producing; when the OD570 is between 0.37 and 0.74 they are moderately producing and when the OD570 is greater than 0.74 they are strongly producing. The error bars indicate the standard error. Dashed lines (- - -) indicate the threshold (cut-off) values at OD570<0.37 and at OD570<0.74.

(Efm5304-IFO) was classified as weakly biofilm-producing while the strain of ERV (Efm5515-IFO) was identified as moderately producing (FIGS. 3C and 4C).

Analysis of the Species-Specific Distribution of the Biofilm Production Phenotype The analysis of biofilm production as a function of the different bacterial species indicates that, among the Gram-negative bacteria, P. aeruginosa had the most consistent biofilm-producing phenotype. In fact, 6 strains (67%) were strongly biofilm-producing, 2 (22%) were moderately biofilm-producing and 1 (11%) was weakly biofilm-producing, respectively (FIG. 3). Conversely, 4 (50%) of the K. pneumoniae isolates were moderately biofilm-producing and 4 strains (50%) proved to be non-adhering/non-producing bacteria. Interestingly, the two clinical isolates and the laboratory strains of R. mannitolilytica had the weakest capacity for adhesion. Among the Gram-positive bacteria, 3 (20%) of the S. aureus strains were strongly biofilm-producing, 5 (50%) were moderately biofilm-producing and 2 were deemed to be weakly biofilm-producing (20%). In the group of clinical isolates of S. epidermis, 6 strains had a weakly biofilm-producing phenotype (75%), while the 2 other strains (25%) were moderately biofilm-producing. Overall, the analysis of the 52 clinical isolates revealed that more than 44% ($^{23}/_{52}$) were strongly/moderately biofilm-producing and 85% ($^{44}/_{52}$) were capable of producing biofilm. Despite the fact that the distribution of these 52 isolates does not reflect clinical reality, this value is in correlation with the 80% estimated by Romling and Balsalobre (Romling, 2012; NIH Parent Grant Announcement, 2002). The most relevant results were obtained with P. aeruginosa (89%) and S. aureus (80%) as the most effective biofilm producers (FIG. 3).

It is interesting to note that the multidrug-resistant strains all proved to belong to the strongly/moderately biofilm-producing groups. Indeed, as indicated previously, multidrug-resistant organisms are more frequently associated with strong biofilm production (Kwon, 2008; Rao, 2008; Sanchez, 2013). This point appears to represent a key element which may promote antimicrobial resistance by selecting highly resistant strains exposed to subinhibitory antimicrobial concentrations and by offering favorable conditions for gene transfer (Wang, 2010).

Categorization with Crystal Violet (CV) Staining

The biofilm production phenotype of the clinical isolates was also evaluated by CV assay. The mean light absorbance for the different biofilm-producing bacteria obtained by analysis with CV is represented in FIG. 6. The results revealed that the reproducibility of the CV assay was generally good with minor differences observed between the means of the results of the repetitions. In the clinical isolates and the reference strains, the biofilm formation was heterogeneous according to the bacterial species and the isolates from the same species.

The results of the CV assay were subsequently compared with the data collected by the process according to the disclosure. Complete agreement was defined as the percentage of isolates which were in the same category with both methods; agreement was considered to be partial when the process according to the disclosure obtained the same classification as the CV OD570±standard deviation. The isolates in disagreement were considered to be inconsistent.

Complete and partial agreement between the characterization process and the CV assay for P. aeruginosa were 83% and 92%, corresponding to two and one disagreements, respectively. For K. pneumoniae, the characterization process showed partial precision of 70% compared to CV staining, with three disagreements. In detail, two strains classified as being in disagreement by the characterization process (Kp3040-IFO; Kp5783-IFO) were classified as weakly biofilm-producing with CV and one moderate strain (Kp0068-IFO) with the characterization process was strongly biofilm-producing according to CV staining. A possible explanation for this reduced agreement for K. pneumoniae could be associated with the production of thick mucus in these strains, which could have partially influenced the agreement between the tests. Indeed, it has been demonstrated that the CV tests may sometimes give false results due to non-specific staining properties (Pan, 2010; Merritt, 2005; Skogman, 2012). The strains of R. mannitolilytica showed 90% agreement between the tests, corresponding to a classification error. Complete agreement between the tests was observed for both S. aureus and S. epidermidis, while for other Gram-positive bacteria the agreement was 87%, corresponding to a classification error (Ef5515-IFO). Overall, complete agreement for Gram-negative strains was 68% while for Gram-positive bacteria it was more than 77%, showing an overall agreement of 72.5% of the samples analyzed. Thus, partial agreement was more than 95%, corresponding to 3 classification errors in 63 strains analyzed. It is important to note that in all the results in disagreement, the classification differs by a single category.

Thus, total agreement was analyzed for the classification process and CV staining using McNemar's test. The results indicate that, for the identifications in disagreement, a statistically significant difference exists between the tests (p=0.007). More precisely, the classification process underestimates the biofilm production compared to CV. This result is entirely unsurprising, since it results from the non-specific staining property of CV. Indeed, crystal violet is known to bind to negatively-charged surface molecules, which are present both on bacteria and the extracellular matrix of the biofilm (Extremina, 2011). This may lead to overestimating the real adhesion capacity of different strains (Pan, 2010; Merritt, 2005; Skogman, 2012).

TABLE 5 overall results for adhesion of the different bacterial species, obtained by the characterization process and CV staining

| Bacterial species | Characterization process | | | | CV staining | | | | Agreement (%) | |
|---|---|---|---|---|---|---|---|---|---|---|
| | Na | W | M | H | Na | W | M | H | Total | Total and partial |
| P. aeruginosa | 0 | 2 | 3 | 7 | 0 | 2 | 3 | 7 | 83 | 100 |
| K. pneumoniae | 5 | 0 | 5 | 0 | 1 | 4 | 3 | 2 | 40 | 80 |
| R. mannitolilytica | 1 | 9 | 0 | 0 | 0 | 10 | 0 | 0 | 80 | 100 |
| S. aureus | 0 | 2 | 6 | 4 | 0 | 1 | 7 | 4 | 92 | 100 |
| S. epidermidis | 0 | 7 | 3 | 0 | 0 | 7 | 2 | 1 | 70 | 100 |
| Other Gram+ | 1 | 3 | 4 | 1 | 0 | 6 | 1 | 2 | 60 | 90 |

Na: non-biofilm-producing,
W: weakly biofilm-producing,
M: moderately biofilm-producing,
H: strongly biofilm-producing Agreement between the characterization process according to the disclosure and CV was measured statistically by the kappa coefficient. The results showed good agreement between the tests for the weak (kappa=0.71±0.09; specificity=94.3%; precision=85.7%), moderate (kappa=0.63±0.11; specificity=84.8%; precision=84.1%) and strong (kappa=0.73±0.10; specificity=97.9%; precision=90.5%) biofilm producers, while for non-adhering/non-producing cells, the agreement was moderate (kappa=0.42±0.2; specificity=91.8%; precision=92.1%). Overall, the strength of agreement between these methods was good (kappa=0.66±0.07), in particular the characterization process demonstrating high levels of specificity and precision (specificity=92.2%; precision=88.1%).

This example therefore clearly demonstrates that the characterization process, also referred to as cBFRT, is a rapid and reliable process for a quantitative evaluation of bacterial biofilm production. This process was tested with different bacterial species, with different biofilm formation phenotypes, including laboratory strains and clinical isolates. The ability of the process to evaluate biofilm production was compared with the CV test, which is a widely used method for biofilm quantification (Christensen, 1985; Stepanovic, 2000, Peeters, 2008). According to the kappa coefficient, the overall agreement between the tests was good (kappa=0.66±0.07) with the process showing high specificity (92.3%) and precision (88.1%) for classifying biofilm-producing bacteria. For all the reference strain results, the process was especially in agreement/consistent with the data reported in the literature. Complete category agreement between the process and CV staining was 72.5% while partial category agreement exceeded 96%, with only two incorrectly classified samples in the 63 strains analyzed. Complete category agreement was 68% for the Gram-negative bacteria and 77% for the Gram-positive bacteria, while partial category agreement was respectively 93.3% and 96.6%. The greatest number of results in disagreement is located in the weakly biofilm-producing/non-adhering group, and, in particular, all these strains exhibited a mucoid phenotype which affected the sensitivity of the CV test. It is worth noting that CV is a non-specific colorimetric assay, which stains living and dead bacteria and also the biofilm matrix. Thus, this test, which merely provides indirect quantification of the biofilm, may lead to overestimation of the results (Pan, 2010; Merritt, 2005; Skogman, 2012), in particular during assay on mucoid strains. Indeed, it has been demonstrated that the overproduction of mucus does not play a significant role in bacterial adhesion and biofilm matrix formation; however, it has a protective role against the host's immune response (Stapper, 2004; Leid, 2005). Conversely, the classification process provides a direct estimation of the true capacity of different bacterial strains to aggregate or adhere, thereby ensuring greater specificity. In fact, the different specificity of the two methods was indirectly confirmed by McNemar's test, which revealed that, in the case in which the methods are in disagreement, the classification process has a significant tendency (p=0.007) to underestimate the results. The other important differences between the classification process and CV are associated with the preparation and the implementation time and also the reproducibility of the data. With the classification process, the preparation of a full plate and inoculation requires for example 30 minutes plus for example five hours of incubation and for example a few minutes for analysis of the plate. Conversely, the CV assay enabled biofilm detection only after 24/48 hours of incubation and requires repeated washing steps and laborious staining procedures (Stepanovic, 2000; Djordjevic, 2002). The requirement for several non-standardized handling operations in the CV test has been associated with large intra- and inter-experimental variations leading to large standard deviations (Peeters, 2008). The lack of reproducibility is also one of the major drawbacks of other conventional techniques, in particular in high-throughput screening (Peeters, 2008).

Nonetheless, the development of standardized methods to identify the phenotype of bacteria is of critical importance in clinical practice, since it may add a key decision-making element to support effective therapeutic management of "difficult infections" such as those associated with surgical devices (namely catheter-associated infections), which often lead to treatment failure and the removal of the apparatus, despite putting in place apparently suitable therapeutic strategies (Costerton, 2003). In fact, once the biofilm is established on the device, the individual cells have an increased tolerance to antimicrobial agents and antibiotic treatment alone is often insufficient. In vitro and in vivo experiments have demonstrated that in a biological biofilm matrix, the cells show a much higher minimum inhibitory concentration (MIC) (approximately 10-1000 times higher) than the same bacterial cells examined under planktonic growth conditions (Høiby, 2011; Hengzhuang, 2012). The effective in vivo antibiotic MIC for eradicating the biofilm may therefore be impossible to achieve by administering antibiotics at doses that appear to be effective for planktonic growth, due to the toxicity and side effects of the medications, including the limitations imposed by renal and/or hepatic function. Thus, the timely recognition of a strong biofilm producer, before the growth of a mature biofilm matrix, may contribute to the appropriate targeting of the therapeutic intervention (type, doses, duration) and decision-making (for example removing the catheter).

As demonstrated, the classification process has been developed to work in combination with traditional microbiological clinical procedures, without altering the daily work routine. Immediately after isolation of the microorganism, for example on an agar plate, it is possible to analyze the biofilm-producing capacity.

As demonstrated in this example, the process of the disclosure makes it possible to characterize biofilm-producing microorganisms, for example bacteria, yeasts etc. It is therefore obvious that the process may be used for characterizing the formation of biofilms by other organisms such as yeasts, with a similar benefit and applications to those claimed for bacteria.

In addition, the classification process may provide information on the capacity of an unknown bacterial isolate to form a biofilm even before the microorganism is identified with conventional phenotyping techniques. Thus, the process according to the disclosure has numerous applications, for example in the field of dentistry, where biofilms are associated with major dental diseases such as tooth decay and periodontal diseases. In addition to these clinical applications, the classification process may represent an invaluable tool for example for the food processing industry and also the sanitation industry, including water systems.

The invention claimed is:

1. A process for determining the biofilm-producing capacity of a microorganism, comprising the following steps:
   a) introducing at least two particles into culture containers comprising a liquid culture medium suited to the growth of said microorganism, said particles resting on a surface submerged in the culture medium,
   b) introducing and independently inoculating the culture medium of the containers obtained in step a) with said microorganism at a concentration range of from $1 \times 10^{-1}$ to $1 \times 10^{-6}$ McFarland (McF) unit, each medium independently comprising a different concentration of microorganisms,
   c) maintaining the inoculated culture media in conditions which enable growth of said microorganism, d) applying a field capable of moving said at least two particles resting on a surface submerged in the culture medium, e) determining the biofilm-producing capacity of the microorganism by observing and measuring the aggregation of said particles as follows:

the absence of aggregation of said particles appearing at a concentration of from $1\times10^{-6}$ to $1\times10^{-4}$ McF corresponding to a strongly biofilm-producing microorganism, the absence of aggregation of said particles appearing from a concentration of greater than $1\times10^{-4}$ and less than $1\times10^{-2}$ McF corresponding to a moderately biofilm-producing microorganism, the absence of aggregation of said particles appearing from a of greater than or equal to $1\times10^{-2}$ McF corresponding to a weakly biofilm-producing microorganism, an aggregation of said particles, regardless of the concentration, corresponding to a non-biofilm-producing microorganism.

2. The process as claimed in claim 1, wherein the process comprises a step e') for determining the Biofilm Index (BFI) value for each of the media by:

analyzing red, green and blue color components of pixels of an image formed by observing the particles, making it possible to determine a particle density per pixel, calculating the correlation between the particles, calculating the aggregation density of the particles expressed as BFI, and determining the biofilm formation potential index per container (BPc) according to the following formula (I):

$$BPc = [1-(BFIe/BFIn)] \tag{I}$$

wherein BFIe corresponds to the biofilm formation index value in the inoculated medium and BFIn corresponds to the biofilm formation index value in a container which does not comprise microorganisms (negative control).

3. The process as claimed in claim 2, comprising a step e'') subsequent to or simultaneous with the step e') for determining the threshold value (S) according to the following formula (II):

$$S = 1-[(mBFIn-3\times stmBFIn)/2]/mBFIn \tag{II}$$

wherein mBFIn is equal to the mean of the BFIs of the negative controls, stmBFIn is equal to the calculated standard deviation of the mean of the BFIs of the negative controls.

4. The process as claimed in claim 3, wherein the biofilm-producing capacity of the microorganism is determined by comparing the BPc value as a function of the concentration of microorganisms, as follows:

a BPc value greater than or equal to the threshold value S from a concentration of microorganisms of from $1\times10^{-6}$ to $1\times10^{-4}$ McF corresponding to a strongly biofilm-producing microorganism, a BPc value greater than or equal to the threshold value S from a concentration of microorganisms of greater than $1\times10^{-4}$ and less than $1\times10^{-2}$ McF corresponding to a moderately biofilm-producing microorganism, a BPc value greater than or equal to the threshold value S from a concentration of microorganisms of $1\times10^{-2}$ McF corresponding to a weakly biofilm-producing microorganism, a BPc value less than the threshold value S, regardless of the concentration, corresponding to a non-biofilm-producing microorganism.

5. A process for classifying microorganisms, comprising the following steps:

a) introducing at least two particles into culture containers comprising a liquid culture medium suited to the growth of said microorganism, said particles resting on a surface submerged in the culture medium, b) introducing and independently inoculating the culture medium of the containers obtained in step a) with said microorganism at a concentration range of from $1\times10^{-1}$ to $1\times10^{-6}$ McF unit, each medium independently comprising a different concentration of microorganisms, c) maintaining the inoculated culture media in conditions which enable growth of said microorganism, d) applying a field capable of moving said at least two particles resting on a surface submerged in the culture medium, with the aim of obtaining an aggregation, in spot form, of said at least two particles, e) classifying the microorganism by observing the aggregation of said particles as follows:

category I: absence of aggregation of said particles appearing at a concentration of from $1\times10^{-6}$ to $1\times10^{-4}$ McF category II: absence of aggregation of said particles appearing from a concentration of greater than $1\times10^{-4}$ and less than $1\times10^{-2}$ McF corresponding to a moderately biofilm-producing microorganism, category III: absence of aggregation of said particles appearing from a concentration of greater than or equal to $1\times10^{-2}$ McF corresponding to a weakly biofilm-producing microorganism, category IV: aggregation of said particles, regardless of the concentration, corresponding to a non-biofilm-producing microorganism.

6. The process as claimed in claim 1, comprising six culture containers in which the concentration of microorganisms at step b) is respectively $1\times10^{-6}$ McF, $1\times10^{-5}$ McF, $1\times10^{-4}$ McF, $1\times10^{-3}$ McF, $1\times10^{-2}$ McF and $1\times10^{-1}$ McF.

7. The process as claimed in claim 1, wherein the inoculated culture media are maintained in conditions which enable growth of said microorganism for 1 to 8 hours.

8. The process as claimed in claim 1, wherein the inoculated culture media are maintained in conditions which enable growth of said microorganism for 5 to 12 generation times of said microorganism.

9. The process as claimed in claim 1, wherein said at least two particles are electrically charged, magnetic or magnetizable particles, or particles covered with at least one magnetic or magnetizable layer.

10. The process as claimed in claim 1, wherein said at least two particles are subjected to an electromagnetic field.

11. The process as claimed in claim 1, wherein said at least two particles are subjected to a gradual increase in the electromagnetic field.

12. The process as claimed in claim 1, wherein said magnetic field is generated by moving field generating means.

13. The process as claimed in claim 1, wherein said at least two particles are illuminated by means of a light source, to detect movement thereof.

14. The process as claimed in claim 1, wherein said at least two particles generate a signal.

15. The process as claimed in claim 14, wherein said at least two particles are excitable, fluorescent or phosphorescent or radioactive or chemiluminescent.

16. The process as claimed in claim 1, wherein one of said containers does not comprise said microorganism, said container representing a control for the medium.

* * * * *